(12) United States Patent
Cashman et al.

(10) Patent No.: US 6,762,052 B1
(45) Date of Patent: Jul. 13, 2004

(54) DNA SEQUENCE ENCODING FLAVIN-CONTAINING MONOOXYGENASE

(76) Inventors: John R. Cashman, 1604 29th Ave. West, Seattle, WA (US) 98199; Noureddine Lomri, 1863 31st Ave., San Francisco, CA (US) 94122

( * ) Notice: Subject to any disclaimer, the term of this patent is extended or adjusted under 35 U.S.C. 154(b) by 0 days.

(21) Appl. No.: 09/583,310

(22) Filed: May 30, 2000

Related U.S. Application Data

(63) Continuation of application No. 08/617,671, filed on Mar. 27, 1996, now abandoned, which is a continuation-in-part of application No. 08/023,843, filed on Feb. 26, 1993, now abandoned.

(51) Int. Cl.[7] ............................. C12N 5/00; C12N 9/02; C12N 15/00; C07H 21/04
(52) U.S. Cl. ................... 435/325; 435/189; 435/320.1; 435/419; 435/252.3; 435/254.11; 536/23.2; 536/23.5
(58) Field of Search ............................. 435/189, 320.1, 435/325, 419, 252.3, 254.11; 536/23.2, 23.5

(56) References Cited

PUBLICATIONS

Sambrook et al. "Molecular Cloning, 2nd Edition", 1989, Cold Spring Harbor Laboratory Press, 17.10–17.27.*
Dolphin, "H. Sapiens mRNA for flavin–containing monooxygenase 3 (FMO3)," *EMBL*, Accession No. Z47552 (1995).
Lomri, et al., *Proc. Natl. Acad. Sci. USA* 92:9910 (1995).
Naeve, et al., "Accuracy of Automated DNA Sequencing: A Multi–Laboratory Comparison of Sequencing Results," *BioTechniques* 19:448–453 (1995).

* cited by examiner

*Primary Examiner*—Rebecca E. Prouty
*Assistant Examiner*—David J. Steadman
(74) *Attorney, Agent, or Firm*—Townsend and Townsend and Crew LLP

(57) ABSTRACT

Novel flavin-containing monooxygenase in substantially pure form is provided. Also disclosed are the cDNA and the reduced amino acid sequences, and fragments and derivatives thereof. The enzymes are useful in metabolism studies, in screening of compounds for biological or pharmacological activity, as well as serving as a bio-indicator of disease states or susceptibility to disease states.

4 Claims, 6 Drawing Sheets

SEQUENCE LISTING

<160> NUMBER OF SEQ ID NOS: 18

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: cDNA probe
      complementary to pig liver FMO

<400> SEQUENCE: 1
ctcatcaagg ggaaagcaaa ggtgtatcca gt                                  32

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: cDNA probe
      complementary to pig liver FMO

<400> SEQUENCE: 2
gaatgttcgg tcccactggg tcatgatgat agcattcct                           39

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: AflIII
      site of 5' HLFMO-3 cDNA

<400> SEQUENCE: 3
ggtaccacat gtccatgggg aagaaag                                        27

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Sal I
      site & 13 NT seq complementary to 3' end HLFMO-3 cDNA

<400> SEQUENCE: 4
gacgtcgacg gatccttagg tcaacaca                                       28

<210> SEQ ID NO 5
<211> LENGTH: 1599
<212> TYPE: DNA
<213> ORGANISM: Homo sapiens
<220> FEATURE:
<221> NAME/KEY: CDS
<222> LOCATION: (1)..(1599)

<400> SEQUENCE: 5

```
atg ggg aag aaa gtg gcc atc att gga gct ggt gtg agt ggc ttg gcc      48
Met Gly Lys Lys Val Ala Ile Ile Gly Ala Gly Val Ser Gly Leu Ala
 1               5                  10                  15 tcc atc agg agc tgt ctg gaa gag ggg ctg gag ccc acc tgc ttt gag      96
Ser Ile Arg Ser Cys Leu Glu Glu Gly Leu Glu Pro Thr Cys Phe Glu
                20                  25                  30 aag agc aat gac att ggg ggc ctg tgg aaa ttt tca gac cat gca gag     144
Lys Ser Asn Asp Ile Gly Gly Leu Trp Lys Phe Ser Asp His Ala Glu
            35                  40                  45
```

-continued

```
gag ggc agg gct agc att tac aaa tca gtc ttt tcc aac tct tcc aaa    192
Glu Gly Arg Ala Ser Ile Tyr Lys Ser Val Phe Ser Asn Ser Ser Lys
 50                  55                  60 gag atg atg tgt ttc cca gac ttc cca ttt ccc gat gac ttc ccc aac    240
Glu Met Met Cys Phe Pro Asp Phe Pro Phe Pro Asp Asp Phe Pro Asn
 65                  70                  75                  80 ttt atg cac aac agc aag atc cag gaa tat atc att gca ttt gcc aaa    288
Phe Met His Asn Ser Lys Ile Gln Glu Tyr Ile Ile Ala Phe Ala Lys
                 85                  90                  95 gaa aag aac ctc ctg aag tac ata caa ttt aag aca ttt gta tcc agt    336
Glu Lys Asn Leu Leu Lys Tyr Ile Gln Phe Lys Thr Phe Val Ser Ser
            100                 105                 110 gta aat aaa cat cct gat ttt gca act act ggc cag tgg gat gtt acc    384
Val Asn Lys His Pro Asp Phe Ala Thr Thr Gly Gln Trp Asp Val Thr
        115                 120                 125 act gaa agg gat ggt aaa aaa gaa tcg gct gtc ttt gat gct gta atg    432
Thr Glu Arg Asp Gly Lys Lys Glu Ser Ala Val Phe Asp Ala Val Met
130                 135                 140 gtt tgt tcc gga cat cat gtg tat ccc aac cta cca aaa aag tcc ttt    480
Val Cys Ser Gly His His Val Tyr Pro Asn Leu Pro Lys Lys Ser Phe
145                 150                 155                 160 cca gga cta aac cac ttt aaa ggc aaa tgc ttc cac agc agg gac tat    528
Pro Gly Leu Asn His Phe Lys Gly Lys Cys Phe His Ser Arg Asp Tyr
                165                 170                 175 aaa gaa cca ggt gta ttc aat gga aag cgt gtc ctg gtg gtt ggc ctg    576
Lys Glu Pro Gly Val Phe Asn Gly Lys Arg Val Leu Val Val Gly Leu
            180                 185                 190 ggg aat tcg ggc tgt gat att gcc aca gaa ctc agc cgc aca gca gaa    624
Gly Asn Ser Gly Cys Asp Ile Ala Thr Glu Leu Ser Arg Thr Ala Glu
        195                 200                 205 cag gtc atg atc agt tcc aga agt ggc tcc tgg gtg atg agc cgg gtc    672
Gln Val Met Ile Ser Ser Arg Ser Gly Ser Trp Val Met Ser Arg Val
210                 215                 220 tgg gac aat ggt tat cct tgg gac atg ctg ctc gtc act cga ttt gga    720
Trp Asp Asn Gly Tyr Pro Trp Asp Met Leu Leu Val Thr Arg Phe Gly
225                 230                 235                 240 acc ttc ctc aag aac aat tta ccg aca gcc atc tct gac tgg ttg tac    768
Thr Phe Leu Lys Asn Asn Leu Pro Thr Ala Ile Ser Asp Trp Leu Tyr
                245                 250                 255 gtg aag cag atg aat gca aga ttc aag cat gaa aac tat ggc ttg atg    816
Val Lys Gln Met Asn Ala Arg Phe Lys His Glu Asn Tyr Gly Leu Met
            260                 265                 270 cct tta aat gga gtc ctg agg aaa gag cct gta ttt aac gat gag ctc    864
Pro Leu Asn Gly Val Leu Arg Lys Glu Pro Val Phe Asn Asp Glu Leu
        275                 280                 285 cca gca agc att ctg tgt ggc att gtg tcc gta aag cct aac gtg aag    912
Pro Ala Ser Ile Leu Cys Gly Ile Val Ser Val Lys Pro Asn Val Lys
290                 295                 300 gaa ttc aca gag acc tcg gcc att ttt gag gat ggg acc ata ttt gag    960
Glu Phe Thr Glu Thr Ser Ala Ile Phe Glu Asp Gly Thr Ile Phe Glu
305                 310                 315                 320 ggc att gac tgt gta atc ttt gca aca ggg tat agt ttt gcc tac ccc   1008
Gly Ile Asp Cys Val Ile Phe Ala Thr Gly Tyr Ser Phe Ala Tyr Pro
                325                 330                 335 ttc ctt gat gag tct atc atc aaa agc aga aac aat gag atc att tta   1056
Phe Leu Asp Glu Ser Ile Ile Lys Ser Arg Asn Asn Glu Ile Ile Leu
            340                 345                 350 ttt aaa gga gta ttt cct cct cta ctt gag aag tca acc ata gca gtg   1104
Phe Lys Gly Val Phe Pro Pro Leu Leu Glu Lys Ser Thr Ile Ala Val
        355                 360                 365
```

-continued

| | | | | | | | | | | | | | | | |
|---|---|---|---|---|---|---|---|---|---|---|---|---|---|---|---|
| att | ggc | ttt | gtc | cag | tcc | ctt | ggg | gct | gcc | att | ccc | aca | gtt | gac | ctc | 1152 |
| Ile | Gly | Phe | Val | Gln | Ser | Leu | Gly | Ala | Ala | Ile | Pro | Thr | Val | Asp | Leu | |
| | 370 | | | | | 375 | | | | | 380 | | | | | |

| cag | tcc | cgc | tgg | gca | gca | caa | gta | ata | aag | gga | act | tgt | act | ttg | cct | 1200 |
| Gln | Ser | Arg | Trp | Ala | Ala | Gln | Val | Ile | Lys | Gly | Thr | Cys | Thr | Leu | Pro | |
| 385 | | | | | 390 | | | | | 395 | | | | | 400 | |

| tct | atg | gaa | gac | atg | atg | aat | gat | att | aat | gag | aaa | atg | gag | aaa | aag | 1248 |
| Ser | Met | Glu | Asp | Met | Met | Asn | Asp | Ile | Asn | Glu | Lys | Met | Glu | Lys | Lys | |
| | | | | 405 | | | | | 410 | | | | | 415 | | |

| cgc | aaa | tgg | ttt | ggc | aaa | agc | gag | acc | ata | cag | aca | gat | tac | att | gtt | 1296 |
| Arg | Lys | Trp | Phe | Gly | Lys | Ser | Glu | Thr | Ile | Gln | Thr | Asp | Tyr | Ile | Val | |
| | | 420 | | | | | 425 | | | | | 430 | | | | |

| tat | atg | gat | gaa | ctc | tcc | tcc | ttc | att | ggg | gca | aag | ccc | aac | atc | cca | 1344 |
| Tyr | Met | Asp | Glu | Leu | Ser | Ser | Phe | Ile | Gly | Ala | Lys | Pro | Asn | Ile | Pro | |
| | | 435 | | | | | 440 | | | | | 445 | | | | |

| tgg | ctg | ttt | ctc | aca | gat | ccc | aaa | ttg | gcc | atg | gaa | gtt | tat | ttt | ggc | 1392 |
| Trp | Leu | Phe | Leu | Thr | Asp | Pro | Lys | Leu | Ala | Met | Glu | Val | Tyr | Phe | Gly | |
| 450 | | | | | 455 | | | | | 460 | | | | | | |

| cct | tgt | agt | ccc | tac | cag | ttt | agg | ctg | gtg | ggc | cca | ggg | cag | tgg | cca | 1440 |
| Pro | Cys | Ser | Pro | Tyr | Gln | Phe | Arg | Leu | Val | Gly | Pro | Gly | Gln | Trp | Pro | |
| 465 | | | | 470 | | | | | 475 | | | | | 480 | | |

| gga | gcc | aga | aat | gcc | ata | ctg | acc | cag | tgg | gac | cgg | tcg | ttg | aaa | ccc | 1488 |
| Gly | Ala | Arg | Asn | Ala | Ile | Leu | Thr | Gln | Trp | Asp | Arg | Ser | Leu | Lys | Pro | |
| | | | | 485 | | | | | 490 | | | | | 495 | | |

| atg | cag | aca | cga | gtg | gtc | ggg | aga | ctt | cag | aag | cct | tgc | ttc | ttt | ttc | 1536 |
| Met | Gln | Thr | Arg | Val | Val | Gly | Arg | Leu | Gln | Lys | Pro | Cys | Phe | Phe | Phe | |
| | | | 500 | | | | | 505 | | | | | 510 | | | |

| cat | tgg | ctg | aag | ctc | ttt | gca | att | cct | att | ctg | tta | atc | gct | gtt | ttc | 1584 |
| His | Trp | Leu | Lys | Leu | Phe | Ala | Ile | Pro | Ile | Leu | Leu | Ile | Ala | Val | Phe | |
| | | 515 | | | | | 520 | | | | | 525 | | | | |

| ctt | gtg | ttg | acc | taa | | | | | | | | | | | | 1599 |
| Leu | Val | Leu | Thr | | | | | | | | | | | | | |
| | 530 | | | | | | | | | | | | | | | |

<210> SEQ ID NO 6
<211> LENGTH: 532
<212> TYPE: PRT
<213> ORGANISM: Homo sapiens

<400> SEQUENCE: 6

Met Gly Lys Lys Val Ala Ile Ile Gly Ala Gly Val Ser Gly Leu Ala
1               5                   10                  15

Ser Ile Arg Ser Cys Leu Glu Glu Gly Leu Glu Pro Thr Cys Phe Glu
            20                  25                  30

Lys Ser Asn Asp Ile Gly Gly Leu Trp Lys Phe Ser Asp His Ala Glu
        35                  40                  45

Glu Gly Arg Ala Ser Ile Tyr Lys Ser Val Phe Ser Asn Ser Ser Lys
    50                  55                  60

Glu Met Met Cys Phe Pro Asp Phe Pro Phe Pro Asp Asp Phe Pro Asn
65                  70                  75                  80

Phe Met His Asn Ser Lys Ile Gln Glu Tyr Ile Ile Ala Phe Ala Lys
                85                  90                  95

Glu Lys Asn Leu Leu Lys Tyr Ile Gln Phe Lys Thr Phe Val Ser Ser
            100                 105                 110

Val Asn Lys His Pro Asp Phe Ala Thr Thr Gly Gln Trp Asp Val Thr
        115                 120                 125

Thr Glu Arg Asp Gly Lys Lys Glu Ser Ala Val Phe Asp Ala Val Met
    130                 135                 140

-continued

```
Val Cys Ser Gly His His Val Tyr Pro Asn Leu Pro Lys Lys Ser Phe
145                 150                 155                 160

Pro Gly Leu Asn His Phe Lys Gly Lys Cys Phe His Ser Arg Asp Tyr
                165                 170                 175

Lys Glu Pro Gly Val Phe Asn Gly Lys Arg Val Leu Val Gly Leu
            180                 185                 190

Gly Asn Ser Gly Cys Asp Ile Ala Thr Glu Leu Ser Arg Thr Ala Glu
            195                 200                 205

Gln Val Met Ile Ser Ser Arg Ser Gly Ser Trp Val Met Ser Arg Val
    210                 215                 220

Trp Asp Asn Gly Tyr Pro Trp Asp Met Leu Leu Val Thr Arg Phe Gly
225                 230                 235                 240

Thr Phe Leu Lys Asn Asn Leu Pro Thr Ala Ile Ser Asp Trp Leu Tyr
                245                 250                 255

Val Lys Gln Met Asn Ala Arg Phe Lys His Glu Asn Tyr Gly Leu Met
                260                 265                 270

Pro Leu Asn Gly Val Leu Arg Lys Glu Pro Val Phe Asn Asp Glu Leu
            275                 280                 285

Pro Ala Ser Ile Leu Cys Gly Ile Val Ser Val Lys Pro Asn Val Lys
290                 295                 300

Glu Phe Thr Glu Thr Ser Ala Ile Phe Glu Asp Gly Thr Ile Phe Glu
305                 310                 315                 320

Gly Ile Asp Cys Val Ile Phe Ala Thr Gly Tyr Ser Phe Ala Tyr Pro
                325                 330                 335

Phe Leu Asp Glu Ser Ile Ile Lys Ser Arg Asn Asn Glu Ile Ile Leu
            340                 345                 350

Phe Lys Gly Val Phe Pro Pro Leu Glu Lys Ser Thr Ile Ala Val
            355                 360                 365

Ile Gly Phe Val Gln Ser Leu Gly Ala Ala Ile Pro Thr Val Asp Leu
    370                 375                 380

Gln Ser Arg Trp Ala Ala Gln Val Ile Lys Gly Thr Cys Thr Leu Pro
385                 390                 395                 400

Ser Met Glu Asp Met Met Asn Asp Ile Asn Glu Lys Met Glu Lys Lys
                405                 410                 415

Arg Lys Trp Phe Gly Lys Ser Glu Thr Ile Gln Thr Asp Tyr Ile Val
            420                 425                 430

Tyr Met Asp Glu Leu Ser Ser Phe Ile Gly Ala Lys Pro Asn Ile Pro
            435                 440                 445

Trp Leu Phe Leu Thr Asp Pro Lys Leu Ala Met Glu Val Tyr Phe Gly
450                 455                 460

Pro Cys Ser Pro Tyr Gln Phe Arg Leu Val Gly Pro Gly Gln Trp Pro
465                 470                 475                 480

Gly Ala Arg Asn Ala Ile Leu Thr Gln Trp Asp Arg Ser Leu Lys Pro
                485                 490                 495

Met Gln Thr Arg Val Val Gly Arg Leu Gln Lys Pro Cys Phe Phe Phe
            500                 505                 510

His Trp Leu Lys Leu Phe Ala Ile Pro Ile Leu Leu Ile Ala Val Phe
            515                 520                 525

Leu Val Leu Thr
            530

<210> SEQ ID NO 7
<211> LENGTH: 1599
```

-continued

```
<212> TYPE: DNA
<213> ORGANISM: Homo sapiens
<220> FEATURE:
<221> NAME/KEY: CDS
<222> LOCATION: (1)..(1599)

<400> SEQUENCE: 7 atg ggg aag aaa gtg gcc atc att gga gct ggt gtg agt ggc ttg gcc      48
Met Gly Lys Lys Val Ala Ile Ile Gly Ala Gly Val Ser Gly Leu Ala
 1               5                  10                  15 tcc atc agg agc tgt ctg gaa gag ggg ctg gag ccc acc tgc ttt gag      96
Ser Ile Arg Ser Cys Leu Glu Glu Gly Leu Glu Pro Thr Cys Phe Glu
             20                  25                  30 aag agc aat gac att ggg ggc ctg tgg aaa ttt tca gac cat gca gag     144
Lys Ser Asn Asp Ile Gly Gly Leu Trp Lys Phe Ser Asp His Ala Glu
         35                  40                  45 gag ggc agg gct agc att tac aaa tca gtc ttt tcc aac tct tcc aaa     192
Glu Gly Arg Ala Ser Ile Tyr Lys Ser Val Phe Ser Asn Ser Ser Lys
     50                  55                  60 gag atg atg tgt ttc cca gac ttc cca ttt ccc gat gac ttc ccc aac     240
Glu Met Met Cys Phe Pro Asp Phe Pro Phe Pro Asp Asp Phe Pro Asn
 65                  70                  75                  80 ttt atg cac aac agc aag atc cag gaa tat atc att gca ttt gcc aaa     288
Phe Met His Asn Ser Lys Ile Gln Glu Tyr Ile Ile Ala Phe Ala Lys
                 85                  90                  95 gaa aag aac ctc ctg aag tac ata caa ttt aag aca ttt gta tcc agt     336
Glu Lys Asn Leu Leu Lys Tyr Ile Gln Phe Lys Thr Phe Val Ser Ser
            100                 105                 110 gta aat aaa cat cct gat ttt gca act act ggc cag tgg gat gtt acc     384
Val Asn Lys His Pro Asp Phe Ala Thr Thr Gly Gln Trp Asp Val Thr
        115                 120                 125 act gaa agg gat ggt aaa aaa gaa tcg gct gtc ttt gat gct gta atg     432
Thr Glu Arg Asp Gly Lys Lys Glu Ser Ala Val Phe Asp Ala Val Met
    130                 135                 140 gtt tgt tcc gga cat cat gtg tat ccc aac cta cca aaa gag tcc ttt     480
Val Cys Ser Gly His His Val Tyr Pro Asn Leu Pro Lys Glu Ser Phe
145                 150                 155                 160 cca gga cta aac cac ttt aaa ggc aaa tgc ttc cac agc agg gac tat     528
Pro Gly Leu Asn His Phe Lys Gly Lys Cys Phe His Ser Arg Asp Tyr
                165                 170                 175 aaa gaa cca ggt gta ttc aat gga aag cgt gtc ctg gtg gtt ggc ctg     576
Lys Glu Pro Gly Val Phe Asn Gly Lys Arg Val Leu Val Val Gly Leu
            180                 185                 190 ggg aat tcg ggc tgt gat att gcc aca gaa ctc agc cgc aca gca gaa     624
Gly Asn Ser Gly Cys Asp Ile Ala Thr Glu Leu Ser Arg Thr Ala Glu
        195                 200                 205 cag gtc atg atc agt tcc aga agt ggc tcc tgg gtg atg agc cgg gtc     672
Gln Val Met Ile Ser Ser Arg Ser Gly Ser Trp Val Met Ser Arg Val
    210                 215                 220 tgg gac aat ggt tat cct tgg gac atg ctg ctc gtc act cga ttt gga     720
Trp Asp Asn Gly Tyr Pro Trp Asp Met Leu Leu Val Thr Arg Phe Gly
225                 230                 235                 240 acc ttc ctc aag aac aat tta ccg aca gcc atc tct gac tgg ttg tac     768
Thr Phe Leu Lys Asn Asn Leu Pro Thr Ala Ile Ser Asp Trp Leu Tyr
                245                 250                 255 gtg aag cag atg aat gca aga ttc aag cat gaa aac tat ggc ttg atg     816
Val Lys Gln Met Asn Ala Arg Phe Lys His Glu Asn Tyr Gly Leu Met
            260                 265                 270 cct tta aat gga gtc ctg agg aaa gag cct gta ttt aac gat gag ctc     864
Pro Leu Asn Gly Val Leu Arg Lys Glu Pro Val Phe Asn Asp Glu Leu
        275                 280                 285
```

-continued

```
cca gca agc att ctg tgt ggc att gtg tcc gta aag cct aac gtg aag        912
Pro Ala Ser Ile Leu Cys Gly Ile Val Ser Val Lys Pro Asn Val Lys
    290                 295                 300 gaa ttc aca gag acc tcg gcc att ttt gag gat ggg acc ata ttt gag        960
Glu Phe Thr Glu Thr Ser Ala Ile Phe Glu Asp Gly Thr Ile Phe Glu
305                 310                 315                 320 ggc att gac tgt gta atc ttt gca aca ggg tat agt ttt gcc tac ccc       1008
Gly Ile Asp Cys Val Ile Phe Ala Thr Gly Tyr Ser Phe Ala Tyr Pro
                325                 330                 335 ttc ctt gat gag tct atc atc aaa agc aga aac aat gag atc att tta       1056
Phe Leu Asp Glu Ser Ile Ile Lys Ser Arg Asn Asn Glu Ile Ile Leu
            340                 345                 350 ttt aaa gga gta ttt cct cct cta ctt gag aag tca acc ata gca gtg       1104
Phe Lys Gly Val Phe Pro Pro Leu Leu Glu Lys Ser Thr Ile Ala Val
        355                 360                 365 att ggc ttt gtc cag tcc ctt ggg gct gcc att ccc aca gtt gac ctc       1152
Ile Gly Phe Val Gln Ser Leu Gly Ala Ala Ile Pro Thr Val Asp Leu
    370                 375                 380 cag tcc cgc tgg gca gca caa gta ata aag gga act tgt act ttg cct       1200
Gln Ser Arg Trp Ala Ala Gln Val Ile Lys Gly Thr Cys Thr Leu Pro
385                 390                 395                 400 tct atg gaa gac atg atg aat gat att aat gag aaa atg gag aaa aag       1248
Ser Met Glu Asp Met Met Asn Asp Ile Asn Glu Lys Met Glu Lys Lys
                405                 410                 415 cgc aaa tgg ttt ggc aaa agc gag acc ata cag aca gat tac att gtt       1296
Arg Lys Trp Phe Gly Lys Ser Glu Thr Ile Gln Thr Asp Tyr Ile Val
            420                 425                 430 tat atg gat gaa ctc tcc tcc ttc att ggg gca aag ccc aac atc cca       1344
Tyr Met Asp Glu Leu Ser Ser Phe Ile Gly Ala Lys Pro Asn Ile Pro
        435                 440                 445 tgg ctg ttt ctc aca gat ccc aaa ttg gcc atg gaa gtt tat ttt ggc       1392
Trp Leu Phe Leu Thr Asp Pro Lys Leu Ala Met Glu Val Tyr Phe Gly
    450                 455                 460 cct tgt agt ccc tac cag ttt agg ctg gtg ggc cca ggg cag tgg cca       1440
Pro Cys Ser Pro Tyr Gln Phe Arg Leu Val Gly Pro Gly Gln Trp Pro
465                 470                 475                 480 gga gcc aga aat gcc ata ctg acc cag tgg gac cgg tcg ttg aaa ccc       1488
Gly Ala Arg Asn Ala Ile Leu Thr Gln Trp Asp Arg Ser Leu Lys Pro
                485                 490                 495 atg cag aca cga gtg gtc ggg aga ctt cag aag cct tgc ttc ttt ttc       1536
Met Gln Thr Arg Val Val Gly Arg Leu Gln Lys Pro Cys Phe Phe Phe
            500                 505                 510 cat tgg ctg aag ctc ttt gca att cct att ctg tta atc gct gtt ttc       1584
His Trp Leu Lys Leu Phe Ala Ile Pro Ile Leu Leu Ile Ala Val Phe
        515                 520                 525 ctt gtg ttg acc taa                                                    1599
Leu Val Leu Thr
    530
```

<210> SEQ ID NO 8
<211> LENGTH: 532
<212> TYPE: PRT
<213> ORGANISM: Homo sapiens

<400> SEQUENCE: 8

```
Met Gly Lys Lys Val Ala Ile Ile Gly Ala Gly Val Ser Gly Leu Ala
1               5                   10                  15

Ser Ile Arg Ser Cys Leu Glu Glu Gly Leu Glu Pro Thr Cys Phe Glu
            20                  25                  30
```

```
Lys Ser Asn Asp Ile Gly Gly Leu Trp Lys Phe Ser Asp His Ala Glu
         35                  40                  45

Glu Gly Arg Ala Ser Ile Tyr Lys Ser Val Phe Ser Asn Ser Ser Lys
     50                  55                  60

Glu Met Met Cys Phe Pro Asp Phe Pro Phe Pro Asp Asp Phe Pro Asn
 65                  70                  75                  80

Phe Met His Asn Ser Lys Ile Gln Glu Tyr Ile Ile Ala Phe Ala Lys
                 85                  90                  95

Glu Lys Asn Leu Leu Lys Tyr Ile Gln Phe Lys Thr Phe Val Ser Ser
             100                 105                 110

Val Asn Lys His Pro Asp Phe Ala Thr Thr Gly Gln Trp Asp Val Thr
         115                 120                 125

Thr Glu Arg Asp Gly Lys Lys Glu Ser Ala Val Phe Asp Ala Val Met
     130                 135                 140

Val Cys Ser Gly His His Val Tyr Pro Asn Leu Pro Lys Glu Ser Phe
145                 150                 155                 160

Pro Gly Leu Asn His Phe Lys Gly Lys Cys Phe His Ser Arg Asp Tyr
                 165                 170                 175

Lys Glu Pro Gly Val Phe Asn Gly Lys Arg Val Leu Val Val Gly Leu
             180                 185                 190

Gly Asn Ser Gly Cys Asp Ile Ala Thr Glu Leu Ser Arg Thr Ala Glu
         195                 200                 205

Gln Val Met Ile Ser Ser Arg Ser Gly Ser Trp Val Met Ser Arg Val
     210                 215                 220

Trp Asp Asn Gly Tyr Pro Trp Asp Met Leu Leu Val Thr Arg Phe Gly
225                 230                 235                 240

Thr Phe Leu Lys Asn Asn Leu Pro Thr Ala Ile Ser Asp Trp Leu Tyr
                 245                 250                 255

Val Lys Gln Met Asn Ala Arg Phe Lys His Glu Asn Tyr Gly Leu Met
             260                 265                 270

Pro Leu Asn Gly Val Leu Arg Lys Glu Pro Val Phe Asn Asp Glu Leu
         275                 280                 285

Pro Ala Ser Ile Leu Cys Gly Ile Val Ser Val Lys Pro Asn Val Lys
     290                 295                 300

Glu Phe Thr Glu Thr Ser Ala Ile Phe Glu Asp Gly Thr Ile Phe Glu
305                 310                 315                 320

Gly Ile Asp Cys Val Ile Phe Ala Thr Gly Tyr Ser Phe Ala Tyr Pro
                 325                 330                 335

Phe Leu Asp Glu Ser Ile Ile Lys Ser Arg Asn Asn Glu Ile Ile Leu
             340                 345                 350

Phe Lys Gly Val Phe Pro Pro Leu Leu Glu Lys Ser Thr Ile Ala Val
         355                 360                 365

Ile Gly Phe Val Gln Ser Leu Gly Ala Ala Ile Pro Thr Val Asp Leu
     370                 375                 380

Gln Ser Arg Trp Ala Ala Gln Val Ile Lys Gly Thr Cys Thr Leu Pro
385                 390                 395                 400

Ser Met Glu Asp Met Met Asn Asp Ile Asn Glu Lys Met Glu Lys Lys
                 405                 410                 415

Arg Lys Trp Phe Gly Lys Ser Glu Thr Ile Gln Thr Asp Tyr Ile Val
             420                 425                 430

Tyr Met Asp Glu Leu Ser Ser Phe Ile Gly Ala Lys Pro Asn Ile Pro
         435                 440                 445

Trp Leu Phe Leu Thr Asp Pro Lys Leu Ala Met Glu Val Tyr Phe Gly
```

-continued

```
                    450                 455                 460
Pro Cys Ser Pro Tyr Gln Phe Arg Leu Val Gly Pro Gly Gln Trp Pro
465                 470                 475                 480

Gly Ala Arg Asn Ala Ile Leu Thr Gln Trp Asp Arg Ser Leu Lys Pro
                485                 490                 495

Met Gln Thr Arg Val Val Gly Arg Leu Gln Lys Pro Cys Phe Phe Phe
                500                 505                 510

His Trp Leu Lys Leu Phe Ala Ile Pro Ile Leu Ile Ala Val Phe
            515                 520                 525

Leu Val Leu Thr
        530

<210> SEQ ID NO 9
<211> LENGTH: 7
<212> TYPE: DNA
<213> ORGANISM: Homo sapiens

<400> SEQUENCE: 9 accatgg                                                               7

<210> SEQ ID NO 10
<211> LENGTH: 6
<212> TYPE: DNA
<213> ORGANISM: Homo sapiens

<400> SEQUENCE: 10 attaaa                                                                6

<210> SEQ ID NO 11
<211> LENGTH: 6
<212> TYPE: DNA
<213> ORGANISM: Homo sapiens

<400> SEQUENCE: 11 aataaa                                                                6

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: HLFM03 -
      Putative FAD binding domain.

<400> SEQUENCE: 12

Gly Ala Gly Val Ser Gly
  1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: NADP+
      binding domain HLFM03

<400> SEQUENCE: 13

Gly Leu Gly Asn Ser Gly
  1               5

<210> SEQ ID NO 14
<211> LENGTH: 35
<212> TYPE: DNA
```

```
-continued

<213> ORGANISM: Artificial Sequence
<220> FEATURE:
<223> OTHER INFORMATION: Description of Artificial Sequence: HFMO 3 cDNA
      primer

<400> SEQUENCE: 14
atcgctcctc tcaaagcagg tgggctccag ccttc                              35

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: HFM 3 cDNA
      primer

<400> SEQUENCE: 15
gggaagaaag tggccatc                                                 18

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: HFMO 3
      oligonucleotide

<400> SEQUENCE: 16
ccggtcgacg gatccaagct taggtcaaca caagg                              35

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: HFMO 3
      oligonucleotide

<400> SEQUENCE: 17
cctggaaagg actgttttgg taggttggg                                     29

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: HFMO 3
      oligonucleotide

<400> SEQUENCE: 18
cctggaaagg actcttttgg taggttggg                                     29
```

DNA SEQUENCE ENCODING FLAVIN-CONTAINING MONOOXYGENASE

RELATED APPLICATIONS

This application is a continuation of and claims the benefit of U.S. patent application Ser. No. 08/617,671, filed Mar. 27, 1996, now abandoned, which is a continuation-in-part of U.S. patent application Ser. No. 08/023,843, filed Feb. 26, 1993, now abandoned, the disclosures of which are incorporated herein by reference in their entirety.

GOVERNMENT SUPPORT

The U.S. government may have certain rights in the invention pursuant to grant GM 36426 received from the U.S. National Institutes of Health.

FIELD OF THE INVENTION

The present invention relates to the drug screening, diagnostic, and synthesis uses of the first recombinant derived adult human liver flavin-containing monooxygenase (form 3), also referred to as adult human liver FMO (form 3) or HLFMO 3.

BACKGROUND AND INTRODUCTION TO THE INVENTION

The mammalian flavin-containing monooxygenase (FMO, EC 1.14.13.8, Dimethylaniline N-oxidase) is a widely distributed enzyme that catalyzes the NADPH-dependent oxygenation of a wide variety of nucleophilic nitrogen-, sulfur-, and phosphorous-containing drugs, chemicals, and xenobiotics (Cashman, Chem. Res. Toxicol. 8:165–181 (1995); Ziegler, Enzymatic Basis of Detoxication 1:201–225 (1980); and Ziegler, Drug Metab. Rev. 6:1–32 (1988)). To dates, many of the investigations examining hepatic FMO have been performed with animal tissues, possibly because of the thermal instability of adult human liver FMO preparations. In contrast to adult human liver cytochromes P-450, almost nothing is known about the structure of adult human liver FMO. Adult human liver FMO has been designated FMO3 (Lawton et al., Arch. Biochem. Biophys. 308: 254–257 (1994)). A few studies with adult human liver microsomes have demonstrated FMO-like enzyme activity (Gold et al., Xenobiotica 3:179–189 (1973) Lemoine et al., Arch. Biochem. Biophys. 276:336–342 (1990); McManus et al., Drug Metab. Dispos. 15:256–261 (1987)) and immunoreactivity with the antibody against pig liver FMO1 (Lemoine et al., Arch. Biochem. Biophys. 276:336–342 (1990); Dannan et al., Mol. Pharmacol. 22:787–794 (1982)). Dimethylaniline N-oxygenation was observed in adult (Gold et al., Xenobiotica 3:179–189 (1973)) and fetal (Rane, Clin. Pharmacol. Ther. 15:32–38 (1973)) human liver microsome preparations. In contrast to dimethylaniline N-oxygenation, which was observed in both kidney and liver tissues, imipramine N-oxygenation was only observed in microsome preparations from human kidney, but not from human liver (Lemoine et al., Arch. Biochem. Biophys. 276:336–342 (1990)). The conclusion from these studies was that FMO was present in human liver tissue, albeit with low specific activity and possibly as multiple enzyme forms. This has been verified with the cloning of five forms of FMO cDNA from human liver cDNA libraries (Phillips et al., Chem. Biol. Interact. 96:17–32 (1995)).

In animals, FMO has been reported to be present as at least one pulmonary form (Williams et al., Biochem. Biophys. Res. Commun. 124:116–122 (1984); Tynes et al., Biochem. Biophys. Res. Commun. 126:1069–1075 (1985)) and as two or more hepatic forms (e.g., forms 1 and 3) (Yamada et al., Arch. Biochem. Biophys. 280:305–312 (1990); Ozols, J. Biol. Chem. 265:10289–10299 (1990)). It is more recently recognized that FMOs are present in multiple tissues and "hepatic" and "pulmonary" forms are misnomers. In rabbit liver, form 1 and 3 are only 55% identical to one another, but the amino acid sequence identity between hog liver FMO1 and rabbit liver FMO form 1 is approximately 87% (Ozols, Arch. Biochem. Biophys. 290:103–115 (1991)). Although studies are limited, forms 1 and 3 FMO apparently differ in many important properties including substrate specificity (Yamada et al., Arch. Biochem. Biophys. 280:305–312 (1990)), enzyme stability (Ozols, Arch. Biochem. Biophys. 290:103–115 (1991)) and other physical properties.

For example, hepatic form 1 FMO activity is stimulated by primary aliphatic alkylamines and form 1 FMO catalyzes the N-oxygenation of secondary and tertiary amines (Ziegler, Enzymatic Basis of Detoxication 1, 201–225 (1980)). In contrast, form 3 FMO apparently N-oxygenates primary aliphatic alkylamines as well as secondary and tertiary amines (Yamada et al., Arch. Biochem. Biophys. 280:305–312. (1990)). Aliphatic primary amines are sequentially N-oxygenated by FMO3 to hydroxylamine and oximes. The pharmacological activity of these metabolities are largely unknown but if FMO3 catalyzes efficient oxime formation from endogenous amines, this could be important in cellular homeostasis. Abnormal amine metabolism by FMO3 could be important in numerous disease states that are associated with abnormal amine metabolism. Some aliphatic tertiary amines such as chlorpromazine are preferentially N-oxygenated by form 3 FMO (Yamada et al., Arch. Biochem. Biophys. 280:305–312 (1990)) but a detailed description of animal FMO3 activity has not been described.

FMO has been purified to homogeneity from a number of sources (Ziegler, Drug Metab. Rev. 19:1–32 (1988)) and it is the pig liver enzyme (FMO form I) which has been the subject of the most extensive studies. Using probes directed against the pig liver FMO and using a fetal human liver cDNA library, a cDNA encoding a FMO has been cloned (Dolphin et al., J. Biol. Chem. 266:12379–12385 (1991)). Thus, fetal human liver flavin-containing monooxygenase (FMO) shares approximately 86% identity with pig liver FMO and 87% identity with rabbit liver FMO form I deduced from the cDNA data (ibid.). Fetal human liver FMO has been designated form 1. Substrate specificity differences are apparent for hepatic form 1 and 3 FMOs from in vitro animal liver enzyme studies (Yamada et al., Arch. Biochem. Biophys. 280:305–312 (1990)), but almost nothing is known about the human liver enzymes.

A number of studies have shown that adult human liver microsomes are capable of tertiary amine N-oxygenation (Gold & Ziegler, Xenobiotica 3:179–189 (1973); McManus et al., Drug Metab. Dispos. 15:256–261 (1987); Lemoine et al., Arch. Biochem. Biophys. 276:336–342 (1990); Rane, Clin. Pharmacol. Ther. 15:32–38 (1973)) and thiobenzamide S-oxygenation (McManus et al., Drug Metab. Dispos. 15:256–261 (1987)).

Adult human liver FMO-dependent N- and S-oxygenation activity is quite thermally labile and activity is maximal at pH 8.4 (Gold and Ziegler, supra; McManus et al., supra; and Lemoine et al., supra, although considerable intersample variation has been observed. Most physical properties of animal FMOs are shared by human liver FMO forms although differences in substrate specificity have not been extensively examined. For example, human liver microsomes did not N-oxygenate imipramine even though imipramine was an excellent substrate for pig liver FMO form I (Lemoine et al., supra). Immunoquantitation of human liver FMO has relied on antibodies directed against animal FMOs. Thus, polyclonal antibodies prepared against pig liver FMO recognized a 60,000 Da human liver protein, although the immunoblot was characterized as very faint. Antisera raised against rat liver FMO recognized an adult human kidney protein, but did not recognize anything in the adult human liver (Lemoine et al., supra (1990)). This is another indication that multiple forms of FMO are present in the adult human liver and kidney.

For over 25 years, the literature has described a few people who, instead of N-oxygenating trimethylamine (TMA) to the polar, readily excreted trimethylamine N-oxide (TMANO), excreted large amounts of unmetabolized TMA in the urine and secreted the volatile and malodorous TMA in their breath, sweat and skin (Humbert, et al., *Lancet* i:770–771 (1970); Higgins et al., *Biochem. Med.* 6:392–396 (1972); Danks et al., *N. Engl. J. Med.* 25:962 (1976)). TMA smells like the essence of rotting fish and people who suffer from this apparent metabolic disorder have what is referred to as the "fish-odor syndrome." In humans, trimethylaminuria is an autosomal recessive disorder involving deficient N-oxygenation of TMA (Al-Waiz et al., *Br. J. Clin. Pharmacol.* 25:664p–665p (1993); Ayesh, et al., *Br. Med. J.*, 655–657 (1993); Ayesh and Smith, *Pharmacol. Ther.* 45:387–401 (1990)). Normally, over 95% of a dose of TMA from dietary sources or otherwise is converted to TMANO that is excreted in the urine. The ability to N-oxygenate TMA is apparently distributed polymorphically (at least in some Caucasian populations evaluated thus far) and people with "fish-odor syndrome" are apparently homozygous for an allele that determines an individuals ability to carry out the N-oxygenation reaction (Ayesh et al., *Br. J. Clin. Pharmacol.* 25:664p–665p (1993). The molecular defect in trimethylaminuria has not yet been defined although it has been attributed to a deficiency in human FMO1 (Dolphin et al., *J. Biol. Chem.* 266:12379–12385 (1991); Dolphin et al., *Biochem J.* 287:261–267 (1992). It is now known, however, in contrast to what has been previously described (Dannan and Guengerich, *Mol. Pharmacol.* 22:787–794 (1982)), that human FMO1 is not expressed to a measurable extent in adult human liver and it is adult humans that have been associated with the disease. It is not likely that other monooxygenases form TMANO from TMA, based on existing studies (Gut and Conney, *Drug Metab. Drug Interacts.* 9:201–208 (1991) and the fact that TMA is a very good substrate for FMO from rat liver (Horori and Benoit, *Biochem. Biophys. Res. Commun.* 212:820–826 (1995). As described herein, cDNA-expressed human FMO3 is a good catalyst for the formation of TMANO from TMA in vitro. It is likely that human FMO3 is largely responsible for the N-oxygenation of TMA.

The deficiency of human FMO3 as an explanation for trimethylaminuria is probably more prevalent than previously realized (Treacy et al., *J. Inher. Dis.* 18:306–312 (1995) and the fish-odor syndrome is a major social handicap to patients who are usually anxious to obtain treatment. In addition to the psychosocial consequences of trimethylaminuria (i.e., anxiety, clinical depression, paranoia, suicidal personality and addiction to cigarettes, alcohol and drugs) on drug and endogenous amine metabolism as a result of altered or deficient human FMO3 activity (Chen and Aiello *Am. J. Med. Genet.* 45:335–339 (1993)), the possibly more important consequences of trimethylaminuria is that it may foretell about other more serious human diseases. For example if human FMO3 is involved in biogenic or other endogenous amine metabolism, a deficiency of human FMO3 may have profound consequences for a wide spectrum of diseases related to abnormal amine metabolism including cardiovascular disease and associated disorders, hypertension, and central nervous system diseases including but not limited to depression, stress, epilepsy, Huntington's, Parkinson's and Alzheimers disease and infectious diseases.

In adult human liver microsomes, in addition to FMO there are numerous other enzymes present including esterases and other monooxygenases. In some cases the other esterases and monooxygenases compete with the adult human liver FMO for substrate activity. For example, an esterase that converts a methyl ester to a carboxylic acid could make that compound unusable as a substrate for the FMO. Other monooxygenases present in the adult human liver could also compete with FMO for substrate activity. Microsomes also generate hydrogen peroxide and alkyl peroxide. Peroxide generated by microsomes could oxidize substrates of FMO such as sulfur, nitrogen, and phosphorous-containing chemicals. Therefore, the presence of such peroxides and other monooxygenases make it difficult to determine the true enzymatic activity and substrate specificity for adult human liver FMO. For this FMO to have any practical use in the research and industrial areas, it must be obtained in a form that is free of human liver microsomal monooxygenases and peroxides generated from these preparations.

SUMMARY OF THE INVENTION

The present invention provides adult human liver flavin-containing monooxygenase (form 3) in substantially pure form. The invention also includes mutants, variants, and fusion products of adult human liver flavin-containing monooxygenase (form 3). The invention also concerns a DNA sequence, and fragments and derivatives thereof, encoding adult human liver flavin-containing monooxygenase (form 3), and host cells involved in the expression of the adult human liver flavin-containing monooxygenase (form 3).

Another aspect of the invention includes methods for in vitro screening of compounds for biological or pharmacological activity. These methods include incubating a monooxygenase with the compound to detect the amount of oxygen consumed, the amount of NADPH consumed, or products formed.

A further aspect of the invention involves methods for detecting cancer in liver cells. This involves generating antibodies that react with the fetal human liver flavin-containing monooxygenase (form 1) and not FMO (form 3). Another method for detecting cancer in liver cells is the use of oligonucleotide probes that bind to the mRNA of the fetal human liver flavin-containing monooxygenase (form 1) and not FMO (form 3) gene. An additional method for detecting liver cancer uses the technique of PCR to amplify the cDNA of the fetal human liver flavin-containing monooxygenase (form 1) gene for hybridization with a probe.

Another aspect of the invention includes a method of selectively oxidizing a nucleophilic compound by incubating a monooxygenase with the nucleophilic compound.

An additional aspect of the invention involves a method of producing a nucleophilic compound with a center of chirality by incubating a monooxygenase with a substrate. This can be coupled in an asymmetric chemi-enzymatic synthesis of a chiral chemical or drug by reacting the resulting oxidized substrate with a strong base and an electiophilic compound.

Another aspect of the invention includes a method of assembling a native or active protein or peptide by incubating a monooxygenase capable of forming disulfides with an unfolded protein or peptide.

A further aspect of the invention involves a method of expressing a monooxygenase in a cDNA expression system to act as a catalyst for the renaturation of proteins or peptides by facilitating disulfide bond formation and protein folding.

DETAILED DESCRIPTION OF THE SPECIFIC EMBODIMENTS

"Expression vectors" refer to vectors which are capable of replicating and transcribing DNA sequences contained therein, where such sequences are linked to other regulatory sequences capable of affecting their expression.

These expression vectors must be propagated in the host organisms or systems either as autonomous episomes or as an integral part of the chromosomal DNA. One form of expression vector which is suitable for use in the invention is the bacteriophage, a virus which replicates in bacteria. The λ-gt11 phage is particularly desirable for this purpose. λ-gt11 is a general recombinant DNA expression vector capable of producing polypeptides specified by the inserted DNA. To minimize degradation, upon induction with a synthetic analog of lactose (IPTG), foreign proteins or portions there of are synthesized as fused proteins with the prokaryotic protein β-galactosidase. The use of host cells defective in protein degradation pathways may also increase the longevity of novel proteins produced from the induced λ-gt11 clones. Proper expression of foreign DNA in λ-gt11 clones will depend upon the proper orientation and reading frame of the inserted DNA with respect to the β-galactosidase gene. Another form of expression vector used in recombinant DNA techniques is the prokaryotic plasmid: an unintegrated (extrachromosomal), double-stranded DNA circle. A third class of expression vectors are the eukaryotic vectors: vectors capable of driving expression of the foreign DNA in a eukaryotic cell. These are generally derived from viral sources and may be either extrachromosomal or integrated. The invention includes any other form of expression vector which serves an equivalent function and which is or subsequently becomes known in the art. Recombinant vectors and methodology disclosed herein are suitable for use in a wide range of prokaryotic and eukaryotic host cells. These host cells include microbial strains, such as E. coli INVlalphaF', Saccharomyces cerevisiae, and cell lines derived from multicellular eukaryotic organisms.

From two adult human cDNA libraries, $2 \times 10^6$ phage plaques were screened with a mixture of three 36-mer synthetic oligonucleotide probes derived from the cDNA sequences of pig liver FMO (Gasser et al., Biochemistry 29:119–124 (1990)).

A total of 5 clones were isolated and purified to homogeneity and mapped by restriction endonuclease digestion. The largest clone which contained approximately 2200 bp (FIG. 1), was subcloned into Bluescript vectors ($KS^{+-}$ and $SK^{+-}$) and both strands were entirely sequenced by the dideoxy method (Sanger et al., Proc. Natl. Acad. Sci. USA 74:5453–5467 (1977)).

Figure 1:
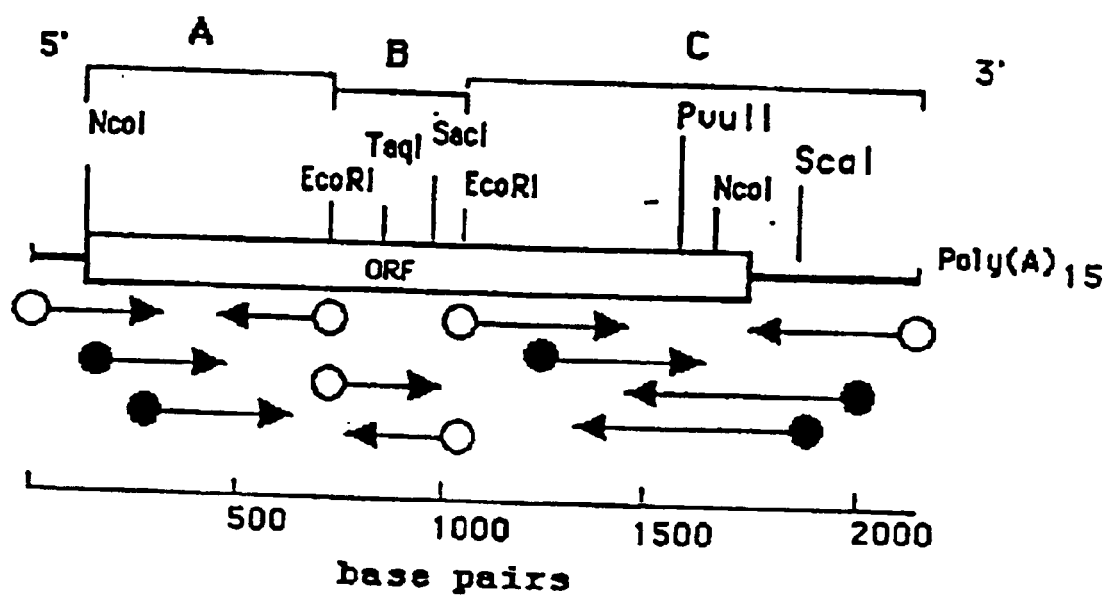
FIG. 1 shows the restriction endonuclease map and sequencing strategy of the HLFMO 3 cDNA insert.
Figure 2:
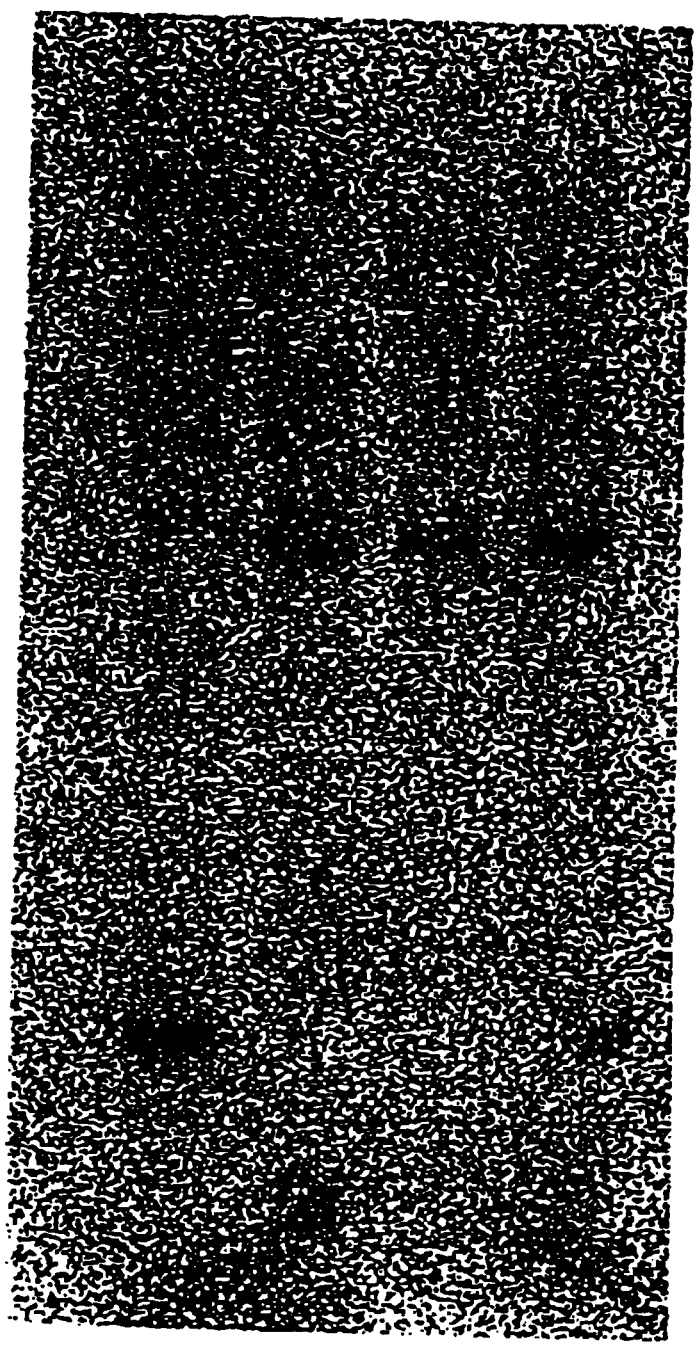
FIG. 2 represents a Southern blot analysis of human genomic DNA using the cDNA fragment of HLFMO 3 as a probe.

Restriction endonuclease map and sequencing strategy of the HLFMO 3 cDNA insert is depicted in FIG. 1. Only the restriction sites used for subcloning are shown. The 1599 nucleotide open reading frame (ORF) is indicated in the box. The 5' and 3' ends of the HLFMO 3 cDNA are shown. The sequencing strategy is indicated by horizontal arrows. The cDNA fragments were subcloned in Bluescript ($KS^{+-}$, $SK^{+-}$) and ordered deletions were produced using Exonuclease III/mung bean nuclease. The deleted and the restriction endonuclease-generated fragments were sequenced by the dideoxy termination method (Sanger et al., Proc. Natl. Acad. Sci. USA 74:5463–5467 (1977)). The letter B indicates the cDNA fragment used as a probe for hybridization analyses (FIG. 2).

The complete nucleotide sequence of the HLFMO 3 cDNA was determined. It contained a 5'-untranslated region of 136 bp, followed by an open reading frame (ORF) of 1599 bp, encoding a protein of Mr 159,179, a termination codon and a 3'-untranslated region of 384 bp. The sequence ACCATGG (SEQ ID No. 9; (bp 134–140)) contained the initiating codon ATG and corresponded to the sequence found to be optimal for initiation of transcription by eukaryotic ribosomes (Kozak, Cell 44, 283–292 (1986)).

Two consensus polyadenylation signals were also found: ATTAA (SEQ ID No. 10) (bp 1805)) and AATAA (SEQ ID No. 11); (bp 2083)), which were situated 15 nucleotides upstream from the poly(A) tail (Breathnach et al., Ann. Rev. Biochem. 50:349–383 (1981)).

The amino acid sequence of adult human liver FMO (form 3) deduced from the cDNA clone is shown in SEQ ID No. 8. Comparison of HLFMO 3 with human liver FMO form 1 (HLFMO 1) (Dolphin et al., J. Biol. Chem. 266:12379–12385 (1991)), pig liver FMO form 1 (PLFMO) (Gasser et al., Biochemistry 29:119–124 (1990)), rabbit liver FMO form 1 (RLFMO I) (Lawton et al., J. Biol. Chem. 265:5855–5861 (1990)) and rabbit lung FMO (RLuFMO) (Lawton et al., J. Biol. Chem. 265:5855–5861 (1990)) showed only a modest degree of primary sequence identity (e.g., 53–57%). HLFMO 3 contained a putative FAD binding domain at amino acid residues 9–14 (e.g., GAGVSG (SEQ ID No. 13)) and a putative $NADP^+$ binding domain at residues 191–196 (e.g., GLGNSG SEQ ID No. 14)). These cofactor-binding regions were highly conserved among all of the mammalian FMO enzymes known as well as the FMO bacterial equivalent, cyclohexanone monooxygenase (Chen et al., J. Bacteriol. 179:781–789 (1988)). In contrast to other mammalian hepatic FMO forms, HLFMO 3 has only a single putative consensus N-glycosylation site (Asn-Xxx-Ser/Thr) at residues 61–63. It was notable that HLFMO 3 did not contain the putative N-glycosylation sites at residues 120–123 and 315–317 that were present in form 1 FMOs.

Adult human liver mRNA was analyzed using the cDNA clone shown in FIG. 1. This cDNA was radiolabeled and the $^{32}$P probe was hybridized to poly(A)$^+$ RNA. The radiolabeled probe detected one mRNA species (2300 bp) in human liver. Genomic DNA extracted from adult human liver was treated with restriction EcoRI (E), PstI (P), BamHI (B) and XhoI (X) (FIG. 2). The samples were fractionated on a 0.7% agarose gel, transferred to a nylon membrane and probed with HLFMO 3 EcoRI B fragment (FIG. 1). As shown in FIG. 2, this probe hybridized to a single band with each sample. The apparent sizes of these bands ranged from 800 bases (EcoRI) to 4000 bases (PstI, BamHI and XhoI).

Currently, evidence for five forms of FMO exist that have deduced amino acid sequences ranging between 52% and 57% identity across species lines (Lawton et al., *Arch. Biochem. Biophys.*, 308:254–257 (1994); Hines et al., *Toxicol. Appl. Pharmacol.*, 125:1–6 (1994)). Thus far, approximately twelve full length sequences of FMO have been reported in the literature of in GENBANK. In addition to the five distinct FMO's (i.e., FMO1, FMO2, FMO3, FMO4 and FMO5), several other published sequences represent orthologs from other species as well as allelic variants.

The screening of animal and human cDNA libraries with other cDNAs or synthetic oligonucleotides encoding FMO have provided cDNA inserts of 2.2–2.6 kb in length or smaller. Thus far, the FMO cDNAs reported in the literature encode for enzymes of approximately 533–535 amino acids but examples of FMOs with nineteen (Atta-Asafo-Adjei et al., *J. Biol. Chem.*, 268:9681–9689 (1993)) or twenty-five (Dolphin et al., *Biochem. J.* 287: 261–267 (1992)) additional C-terminal amino acids have been observed. In addition, minor FMO structural variants have been observed in rabbit liver but the role of the fill variants in rabbit physiology in not known. It is possible that mutations in conserved regions of the five FMOs could lead to enzymes with significantly decreased catalytic or physical properties. To be considered a member of the family of mammalian FMOs, approximately 40% or more amino acid sequences are required to be identical. Related non-mammalian flavoenzymes do not belong to the family of flavoprotein monooxygenases because, for example in the case of cyclohexanone monooxygenase, it is only 25% identical to amino acid sequences of mammalian FMOS. For a particular, FMO to belong to a specific subfamily, the requirement is for the ortholog to have 80% or greater amino acid sequence identity. However, even under optimal conditions, low stringency screening of an adult human liver cDNA library with pig FMO1 did not identify cDNA clones encoding human FMO3. In fact, the screen identified several weakly hybridizing clones, all of which turned out to encode human FMO4 (Phillips et al., *Chem.-Biol. Interacts.* 96:17–32 (1995)). This result is surprising in view of the fact that the human FMO3 is now recognized as the major form of FMO in adult human liver. Clearly, the high stringency procedure employed previously and the quality of the adult human liver library led to the difference in the success of isolation of the adult human FMO3 clones (Lomri et al., *Proc. Natl. Acad Sci. USA* 89:1685–1689 (1992)). The hybridization conditions described in the isolation of human FMO3 clones will selectively hybridize with orthologs only about 95% or greater identity. An analysis of the hybridization melting temperatures of the oligonucleotides used (i.e., oligos PLFMO1 and PLFMO1, see below) employing the following equation: $T_m = [\Delta H/\Delta S + R\ln(C_t)] - 273.15$ showed that the Tm for adult human liver FMO3 was significantly higher that the Tm for the other human liver FMOs now known. Hybridization is detected or it is not (Benton and Davis, *Science* 916:180–182 (1987)). Under the conditions of the salts, temperature-and detergent only the adult human FMO3 was selectively hybridized under the stringent conditions employed.

Some FMO regions are substantially homologous even between families. For example, residues near the N-terminus and between residue 450 and the C-terminus of FMO contain relatively highly conserved regions indicating important amino acid structural and/or functional domains. Creating variants or exchanging one region of FMO with another to maintain over 95% identity can introduce improved catalytic or deisirable physical properties into the newly engineered FMO. On the other hand, some regions of FMO are important to enzyme function such that removal or substitution with unacceptable amino acids may significantly decrease catalytic activity or some other physical property. This is borne out by the highly conserved FAD- and NADP$^+$-binding domains (i.e., GXGXXG) near deduced amino acid positions 9–14 and between 186–196, respectively. Intact NADP$^+$ and FAD cofactor binding domains are essential for FMO function because site-directed mutagenesis of the region 9–14, to GXGXXV, resulted in expression of an inactive protein to which no FAD was bound (Lawton and Philpot, *J.Biol. Chem*. 268:5728–5734 (1993)). Conservative amino acid changes on the N-terminal side of the FAD-binding domain of FMO resulted in an FMO that retained activity. Fusing a 35 amino acid portion of β-galactosidase to the N-terminus of pig FMO1 significantly enhanced the level of expression in *E. coli* while not noticably affecting the specific activity of the enzyme. Other FMO fusion proteins are also very active. For example, the maltose binding protein fusion protein to FMO3 possesses excellent catalytic and physical properties. The N-terminal peptides of FMOs examined to date do not have any clearly discernible signal peptide sequences and, coupled with the presence of an FAD-binding region, does not suggest this region as a functional membrane insertion domain. To date, most of the membrane insertion correlations have focused on highly lipophilic amino acid sequences.

To define the interaction of FMO in the membrane, it was reasoned that the core glycosylation enzyme system required for N-glycosylation was localized to the iuminal side of the endoplasmic reticulum membrane. As most FMOs have a putative consensus N-glycosylation site, determination of the site of N-glycosylation would indicate the region of FMO that was translocated across the endoplasmic membrane. With the exception of FMO4, all FMOs sequenced to date have at least a single putative consensus N-glycosylation site (i.e., Asn-Xaa-Ser/Thr). Based on indirect evidence, it has been reported that pig FMO1 is glycosylated (Korsmeyer et al., *Flavins and Flavoproteins* (Curti, Ronchi and Zanetti, eds.) Walter de Gruyter and Co., Berlin, pp 243–246 (1991)) and subsequent HPLC-mass spectrometry studies showed that a saccharide was attached to Asn 120. The highly conserved nature of the putative consensus N-glycosylation sites indicates that the region has an important structural and/or functional role in enzyme action. Analysis of the distance between the N-glycosylation site and transmembrane hydrophobic segments indicates that the N-glycosylation site of FMO is separated from the membrane by at least 13 amino acid residues. Membrane association likely occurs between amino acid residues Cys 30 and Leu 90, because the NADP$^+$- and FAD-binding domains must be on the same side of the membrane to affect catalysis. A variant of FMO in this region that replaces the membrane association sequence with compatible amino acids can be used to provide a more water-soluble and tractable protein that possesses more desirable catalytic and physical properties. All mammalian FMOs possess very strong membrane association properties and in the highly purified state are extremely intractable proteins with poor solubility characteristics (Guan et al., *Biochemistry* 30:9892–9900 (1991)). For example, even with as many as 200 C-terminal amino acids deleted from rabbit FMO2, membrane association was still observed. Comparison of the amino acids of the 5 forms of FMOs (deduced from cDNA data) by hydropathy profiles shows that many regions of FMO are highly hydrophobic as well as highly conserved. This is true even for regions of the FMO isoform sequence that are only modestly identical (i.e., 25–30% amino acid identity). FMO membrane association is not a passive event dictated exclusively by hydrophobic C-terminal amino acid residues. Rather, the information for active FMO membrane association is believed to be encoded in an internal sequence proximal to the N-terminus that signals membrane association. Modification of the membrane insertion sequence or the substrate binding channel by discrete or random mutagenesis or by discovering naturally occurring variants that heave different amino acids in these regions can also provide FMO enzymes with improved catalytic or physical properties.

The cDNA sequence does not provide information about possible N-terminal modifications and in each case examined (i.e., FMO1, FMO2 and FMO3) the initiation amino acid methionine is not present and the following amino acid is N-acetylated. The results have primarily come from mass spectral studies of the purified proteins. Residues such as alanine or glycine near the N-terminus apparently promote the removal of methionine during FMO protein maturation (Flinta et al., *Eur. J. Biochem.* 154:193–196 (1986)).

In certain instances, one may employ changes in the sequence of recombinant FMO3 and allelic variants to substantially increase or even decrease the biological activity of FMO3, depending on the intended use of the preparation. The biological activity may be determined as demonstrated herein. Homologous sequences, allelic variations, and natural mutants; induced point, deletion, and insertion mutants; alternatively expressed variants; proteins encoded by DNA which hybridize to nucleic acids which encode naturally occurring FMO3 are included herein.

The disclosed sequences of FMO3 are used to identify and isolate FMO polynucleotide molecules from suitable hosts such as canine, ovine, bovine, caprine, lagomorph, avian or the like. Complementary DNA molecules encoding FMO3 may be obtained by constructing a cDNA library mRNA from, for example, liver. DNA molecules encoding FMO3 may be isolated from such a library using the disclosed sequences in standard hybridization techniques (e.g., Sambrook et al. ibid., and Bothwell, Yancopoulos and Alt, eds, *Methods for Cloning and Analysis of Sukarvotic Genes*, Jones and Bartlett Publishers, Boston, Mass. 1990) or by amplification of sequences using polymerase chain reaction (PCR) amplification (e.g, Loh et al. *Science* 243: 217–222, 1989; Frohman et al., *Proc. Acad. Sci. USA* 85: 8998–9002, 1968; and Erlich (ed.), *PCR Technology: Principles and Applications for DNA Amplification*, Stockton Press, 1989; and U.S. Pat. No. 4,683,195, which are incorporated by reference herein in their entirety). In a similar manner, genomic DNA encoding FMO3 is obtained using probes designed from the sequences disclosed herein. Suitable probes for use in identifying FMO 3 sequences are obtained from FMO3-specific sequences, such as those, e.g., that are highly conserved regions. Suitable PCR primers are between 7–50 nucleotides in length, more preferably between 15, sometimes 18–20 and 25 nucleotides in length. Alternatively, FMO3 polynucleotide molecules may be isolated using standard hybridization using probes of at least about 7 nucleotides in length and up to and including the full coding sequence.

The choice of hybridization conditions will generally be guided by the purpose of the hybridization, the type of hybridization (DNA-DNA or DNA-RNA), and the, level of relatedness between the sequences. Methods for hybridization are well established in the literature; See, for example: Sambrook, ibid.; Hames and Higgins, eds, *Nucleic Acid Hybridization A Practical Approach*, IRL Press, Washington D.C., 1985; Berger and Kimmel, eds, *Methods in Enzymology*, Vol. 52, Guide to Molecular Cloning Techniques, Academic Press Inc., New York, N.Y., 1987; and Bothwell, Yancopoulos and Alt, eds, *Methods for Cloning and Analysis of Eukaryotic Genes*, Jones and Bartlett Publishers, Boston, Mass. 1990; which are incorporated by reference herein in their entirety. The stability of nucleic acid duplexes will decrease with an increased number and location of mismatched bases; thus, the stringency of hybridization may be used to maximize or minimize the stability of such duplexes. Hybridization stringency can be altered by: adjusting the temperature of hybridization; adjusting the percentage of helix-destabilizing agents, such as formamide, in the hybridization mix; and adjusting the temperature and salt concentration of the wash solutions. In general, the stringency of hybridization is adjusted during the post-hybridization washes by varying the salt concentration and/or the temperature. Stringency of hybridization may be reduced by reducing the percentage of formamide in the hybridization solution or by decreasing the temperature of the wash solution. High stringency, conditions may involve high temperature hybridization (e.g., 65–68° C. in aqueous solution containing 4–6×SSC, or 42° C. in 50% formamide) combined with washes at high temperature (e.g., 5–25° C. below the $T_m$) at a low salt concentration (e.g., 0.1×SSC). Reduced stringency conditions may involve lower hybridization temperatures (e.g., 35–42° C. in 20–50% formamide) with washes at intermediate temperature (e.g., 40–60° C.) and in a higher salt concentration (e.g., 2–6×SSC). Moderate stringency conditions may involve hybridization at a temperature between 50° C. and 55° C. and washes in 0.1×SSC, 0.1% SDS at between 50° C. and 55° C.

The invention provides isolated and purified polynucleotide molecules encoding FMO3 capable of hybridizing under stringent conditions to an oligonucleotide of 15 or more contiguous nucleotides of SEQ ID NO: 7 or SEQ ID NO: 9 and their complementary strands. The isolated FMO3 polynucleotide molecules preferably encode FMO3 proteins or fragments thereof that have enzymatic activity.

The present invention provides methods for producing recombinant FMO3 by inserting a DNA molecule encoding FMO3 into a suitable expression vector, which is in turn used to transfect or transform a suitable host cell.

Suitable expression vectors for use in carrying out the present invention will generally comprise a promoter capable of directing the transcription of a polynucleotide molecule of interest in a host cell. Representative expression vectors may include both plasmid and/or viral vector sequences. Suitable vectors include retroviral vectors, vaccinia viral in vectors, CMV viral vectors, BLUESCRIPT, baculovirus vectors, and the like. Promoters capable of directing the transcription of a cloned gene or cDNA may be inducible or constitutive promoters and include viral and cellular promoters. For expression in mammalian host cells, suitable viral promoters include the immediate early cytomeglovirus promoter (Boshart et al., *Cell* 41: 521–530, 1985) and the SV40 promoter (Subramani et al., *Mol. Cell. Biol.* 1: 854–864, 1981). Suitable cellular promoters for expression of proteins in mammalian host cells include but are not limited to the mouse metallothionien-1 promoter (Palmiter et al., U.S. Pat. No. 4,579,821), and tetracycline-responsive promoter (Gossen and Bujard, *Proc. Natl. Acad. Sci. USA* 89: 5547–5551, 1992 and Pescini et al., *Biochem. Biophys. Res. Comm.* 202: 1664–1667, 1994). Also contained in the expression vectors is a transcription termination signal located downstream of the coding sequence of interest. Suitable transcription termination signals include the early or late polyadenylation signals from SV40 (Kaufman and Sharp, *Mol. Cell. Biol.* 2:1304–1319, 1982), the polyadenylation signal from the Adenovirus 5 e1B region and the human growth hormone gene terminator (DeNoto et al., *Nucleic Acid. Res.* 9: 3719–3730, 1981).

Mammalian cells may be transfected by a number of methods including calcium phosphate precipitation (Wigler et al., *Cell* 14: 725, 1978; Corsaro and Pearson, *Somatic Cell Genetics* 7: 603, 1981; Graham and Van der Eb, *Virology* 52: 456, 1973); lipofection (Felgner et al., *Proc. Natl. Acad. Sci. USA* 84: 7413–7417, 1987), microinjection and electroporation (Neumann et al., *EMBO J.* 1: 8410845, 1982). Mammalian cells can be transduced with virus such as SV40, CMV and the like. In the case of viral vectors, cloned DNA molecules may be introduced by infection of susceptible cells with viral particles. Retroviral vectors may be preferred for use in expressing FMO3 in mammalian cells, particularly when FMO3 is used in methods of gene therapy (for review, see, Miller et al., *Methods in Enzymology* 217: 581–599, 1994; which is incorporated herein by reference in its entirety).

It may be preferable to use a selectable marker to identify cells that contain the cloned DNA. Selectable markers are generally introduced into the cells along with the cloned DNA molecules and include genes that confer resistance to drugs, such as neomycin, hygromycin and methotrexate. Selectable markers may also complement auxotrophies in the host cell. Yet other selectable markers provide detectable signals, such as beta-galactosidase to identify cells containing the cloned DNA molecules. Selectable markers may be amplifiable. Such amplifiable selectable markers may be used to amplify the number of sequences integrated into the host genome.

As would be evident to one of ordinary skill in the art, the polynucleotide molecules of the present invention may be expressed in *Saccharomyces cerevisiae*, filamentous fungi, and *E. coli*. Methods for expressing cloned genes in *Saccharomyces cerevisiae* are generally known in the art (see, "Gene Expression Technology," *Methods in Enzymoloy*, Vol. 185, Goeddel (ed.), Academic Press, San Diego, Calif., 1990 and "Guide to Yeast Genetics and Molecular Biology," Methods in Enzymology, Guthrie and Fink (eds.), Academic Press, San Diego, Calif., 1991; which are incorporated herein by reference). Filamentous fungi (e.g., strains of Asperpillus) may also be used to express the proteins of the present invention. Methods for expressing genes and cDNAs in cultured mammalian cells and in *E. coli* is discussed in detail in Sambrook et al. (*Molecular Cloning: A Laboratory Manual*, Second Edition, Cold Spring Harbor, N.Y., 1989; which is incorporated herein by reference). As would be evident to one skilled in the art, one could express the protein of the instant invention in other host cells such as avian, insect and plant cells using regulatory sequences, vectors and methods well established in the literature.

FMO3 proteins produced according to the present invention are purified using a number of established methods, such as affinity chromatography using anti-FMO3 antibodies coupled to a solid support and sequence-specific chromatography. Additional purification may be achieved using purification means such as liquid chromatography, gradient centrifugation and gel electrophoresis among others. Methods of protein purification are known in the art (see generally, Scopes, R., *Protein Purification*, Springer-Verlag, N.Y., 1982, which is incorporated herein by reference) and can be applied to the purification of recombinant FMO3 described herein.

Thus, as discussed above, the present invention provides FMO3 isolated from its natural cellular environment, substantially free of other cellular proteins. Purified FMO3 is also provided. Substantially pure FMO3 of at least about 50% is preferred, at least about 70–80% is more preferred, and 95–99% or more homogeneity most preferred. Once purified, partially or to homogeneity, as desired, the recombinant FMO3 or native FMO3 may be used to generate antibodies, in screening and diagnostic procedures, etc.

Expression of Adult Human Liver FMO 3 in *E. Coli*

Figure 3:
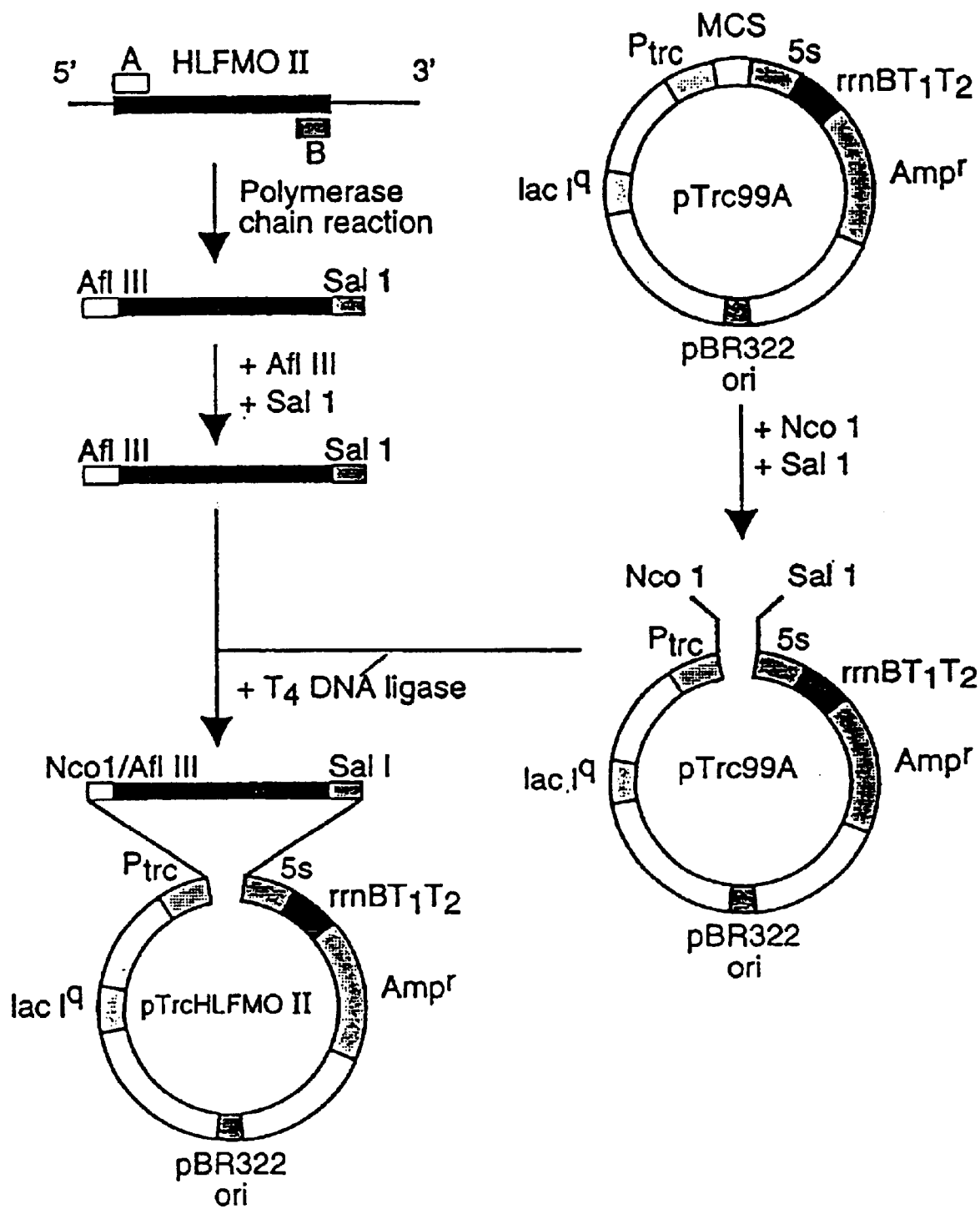
FIG. 3 represents the schematic for the construction of the expression vector pTrcHLFMO 3.
Figure 4:
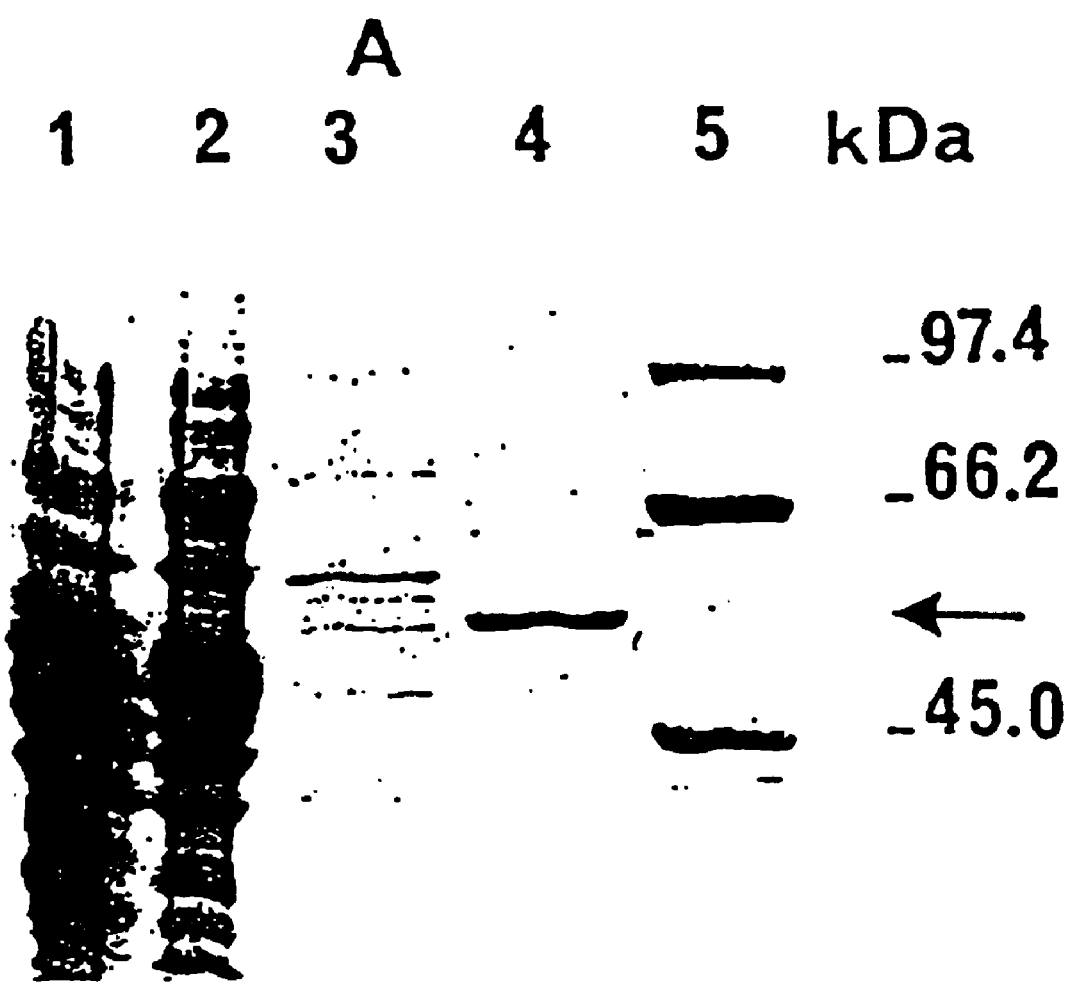
FIG. 4 shows the SDS-PAGE analysis of the products from the expression vector pTrcHLFMO 3.
Figure 5:
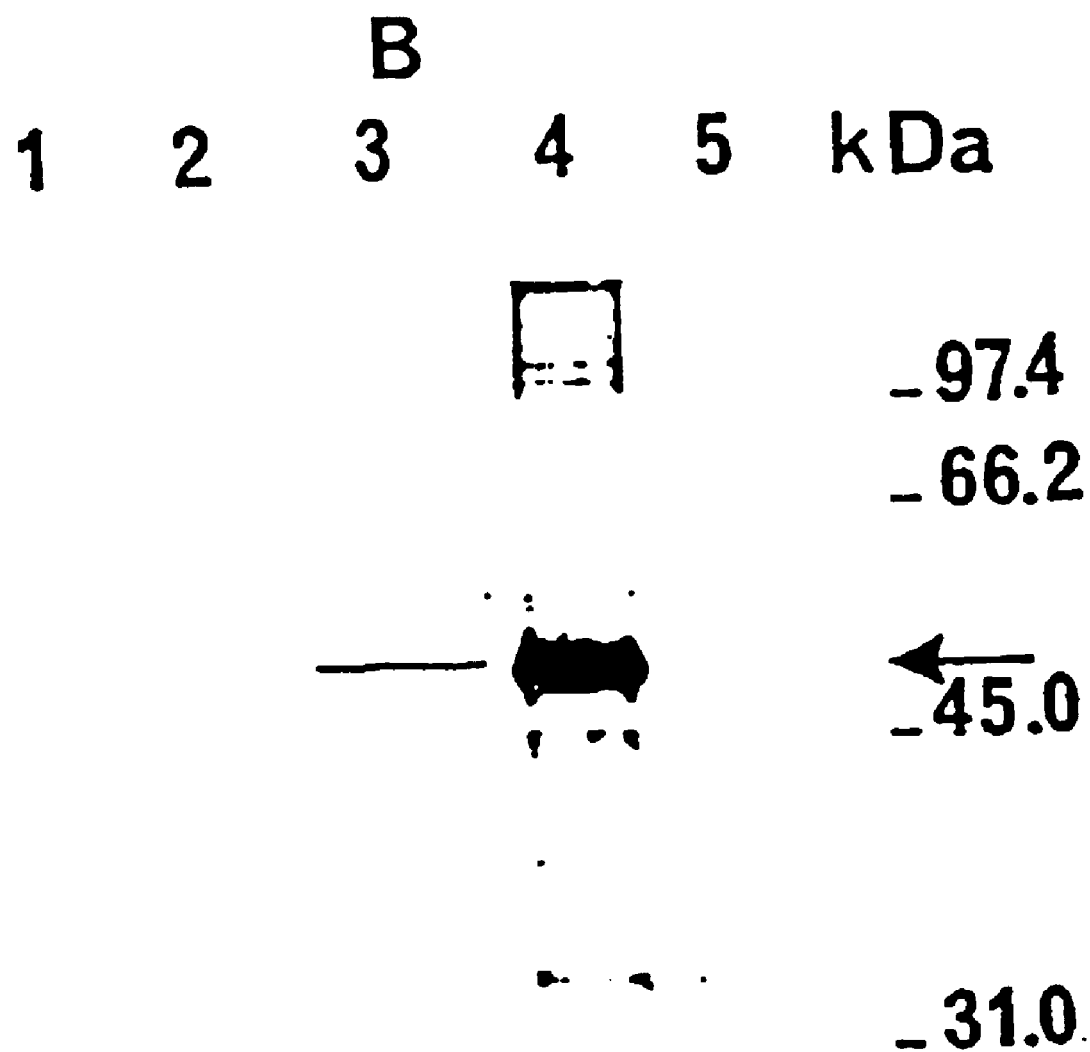
FIG. 5 represents the Western blot analysis of the products from the expression vector pTrcHLFMO 3.

The expression vector was constructed and amplified by PCR by ligating the appropriate components designed to create for the full-length adult human liver FMO (form 3) cDNA as described in Example 6. The PCR product which was designed to obtain the full-length open reading frame cDNA of HLFMO 3 was inserted into a pTrc99A expression vector to give the expression plasmid, pTrcHLFMO 3 (FIG. 3). Restriction enzyme and DNA sequence analyses (Sanger et al., *Proc. Natl. Acad. Sci. USA* 74:5463–5467 (1977)) of the pTrcHLFMO 3 DNA sequence confirmed that the 5'-end of the HLFMO 3 cDNA coding strand was successfully extended and correctly inserted into the pTrc99A vector (FIG. 3). The expression of pTrcHLFMO 3 in the *E. coli* host bacteria NM522 following incubation in the presence of the inducing agent IPTG produced active HLFMO 3. NM522 host bacteria transformed with the pTrc99A vector alone did not produce any detectable FMO activity when grown in the presence or absence of IPTG. As shown in FIG. 4, the IPTG-induced HLFMO 3 protein from lysates of the pTrcHLFMO 3 transformed bacterial cells was detectable on SDS-PAGE. The in solubilized proteins from transformed *E. coli* cells were analyzed by SDS PAGE in duplicate. One gel was used for the analysis by Coomassie-blue staining (FIG. 4) and the other gel was subjected to Western blot analysis using antibodies directed against the guinea pig form 3 FMO (FIG. 5). A band at 60 kDa corresponding to the expressed HFLMO 3 protein was clearly detected. It was estimated that less than it of the total solubilized expressed protein was present as HLFMO 3.

Substrates and Synthesis of N-Oxides and S-Oxides

Trifluoperazine, thiobenzamide and chlorpromazine were purchased from Aldrich Chemical Co. (Milwaukee, Wis.). The 10-(N,N-Dimethylaminoalkyl)-2-(trifluoromethyl) phenothiazines were obtained from Professor D. M. Ziegler (University of Texas, Austin, Tex.) (Nagata et al., *Chem. Res. Toxicol.* 3:372–376 (1990)). 2-Methyl-1,3-benzodithiole was obtained from Professor D. Boyd (The Queens University of Belfast, N. Ireland) (Boyd et al., *J. Chem. Soc. Perkin Trans.* 1:1105 (1992)). (+) and (−)-4-Bromophenyl-1,3-oxathiolane were provided by Professor J. Sandstrom (University of Lund, Sweden). All of the substrates were completely characterized by $^1$H NMR, MS, UV-vis and in some cases circular dichroism spectroscopic means. The synthesis of tertiary amine N-oxides of trifluoperazine and chlorpromazine was accomplished by the general method previously described (Cashman et al., *Drug Metab. Dispos.* 16:616–622 (1988); Sofer & Ziegler, *Drug*

Metab. Dispos. 6:232–239 (1978)). The 10-(N,N-dimethylaminoalkyl)-2-(trifluromethyl)phenothiazine N-oxides were biosynthesized with pig liver microsomes as described before (Nagata et al., *Chem. Res. Toxicol.* 3:372–376 (1990)). All of the tertiary amine N-oxides were completely characterized by spectral means. Similarly, thiobenzamide S-oxide (Cashman & Hanzlik, *J. Org. Chem.* 47, 4645–4650 (1982)), 4-bromophenyl-1,3-oxathiolane S-oxide diastereomers (Andresen et al., 1993), and 2-methyl-1,3-benzodithiole S-oxide diastereomers (Boyd et al., *J. Chem. Soc. Perkin Trans.* 1:1105 (1992)) were synthesized and completely characterized by methods, previously described.

Substrate Oxygenation

The regio- and stereo-selective oxygenation of various chemicals and drugs by human liver microsomes and solubilized protein from *E. coli* cells transformed with pTrcHLFMO 3 were examined to selectively monitor FMO enzyme action as well as to examine possible involvement of cytochromes P-450 or non-enzymatic oxidation of the same substrate. Trifluoperazine, other tricyclic antidepressants and other phenothiazines provided excellent probes for monooxygenase action because these chemicals possess a nucleophilic tertiary amine center known to be selectively oxygenated by FMO (Sofer & Ziegler, *Drug Metab. Dispos.* 6: 232–239 (1978); Nagata et al., *Chem. Res. Toxicol.* 3:.372–376 (1990)) and an electrophilic sulfur atom known to be selectively oxidized by cytochromes P-450 or by non-enzymatic means (i.e., $H_2O_2$ or ROOH)). Other substrates (i.e., thiobenzamide, 4-bromophenyl-1,3-oxathiolane and 2-methyl-1,3-benzothiole) were also examined for S-oxygenation activity. In all cases examined, product formation was directly determined by HPLC analysis of organic extracts.

Solubilized protein from *E. coli* cells transformed with pTrcHLFMO 3 was evaluated for N- and S-oxygenase activity with compound 5 (Nagata et al., *Chem. Res. Toxicol.* 3:372–376 (1990)). In parallel, *E. coli* cells transformed with non-recombinant plasmid pTrc 99A were solubilized with 1-Triton X-100 and centrifuged at 100,000xg to afford a supernatant and a 100,000xg pellet. Solubilization of the recombinant HLFMO 3 protein resulted in 84% N-oxygenase activity (i.e., 0.23 nmol/min/mg of protein) in the supernatant fraction. The pellet contained 16% of the N-oxygenase activity (i.e., 0.043 nmol/min/mg of protein). The non-recombinant solubilized protein did not possess any detectable FMO activity. Other tertiary amine and sulfur-containing substrates examined also gave similar supernatant: pellet FMO activity ratios. No detectable amount of non-enzymatic N-oxygenation was observed during the metabolic incubations examined. In addition, no detectable N-oxide reduction was observed.

Preliminary studies that showed crude homogenates or solubilized protein of transformed *E. coli* supplemented with NADPH catalyzed the S- or N-oxygenation of a variety of substrates. As a standard for comparison, the oxidation of substrates with human liver microsomes was also studied. Under the conditions of the experiments, no detectable amount of non-FMO mediated S- or N-oxygenation was observed. For compound 6, formation of the tertiary amine N-oxide was a linear function of bacterial lysate protein concentration (0–4.6 mg of protein) and of time (0–10 min). In the presence of human liver microsomes, tertiary amine N-oxide formation of compound 6 was a linear function of microsomal protein concentration (0–0.5 mg of protein) and of time (0–30 min) (data not shown). N-Oxygenation of compound 6 was dependent upon the pH of the reaction mixture, and microsomal protein and solubilized bacterial lysate of expressed HLFMO 3 gave virtually identical pH-rate profiles. The pH-optimum for tertiary amine N-oxygenation was approximately 10 and the pH-rate profile resembled a titration curve with the midpoint near a value of pH 9.5. Other sulfur-containing substrates (i.e., thiobenzamide and 4-bromophenyl-1,3-oxathiolane) showed a maximum S-oxygenase activity in the presence of microsomes and expressed HLFMO 3 of approximately pH 8.5. The true pH optimum is probably 8.5 and it is likely that deprotonation of the amines (pka=9.5) provided the nonprotonated substrate and thus influenced the apparent pH optimum of the enzyme.

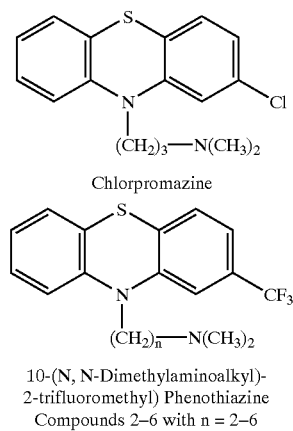

Chlorpromazine 10-(N, N-Dimethylaminoalkyl)-
2-trifluoromethyl) Phenothiazine
Compounds 2–6 with n = 2–6

As shown in Table 1, N-oxygenation of chlorpromazine and compounds 2–4 was detectable, but compounds 5 and 6, with longer side chains, were better substrates for human liver microsomes and solubilized protein from *E. coli* transformed with pTrcHLFMO 3. Dichloromethane extracts of metabolic incubations with microsomes and solubilized protein of selected substrates from transformed *E. coli* were subjected to mass spectral analyses. The liquid secondary ion mass spectra (+LSIMS) of the tertiary amine N-oxide metabolite of compounds isolated from pig liver microsomes was similar with the chemical ionization (CI) spectrum of the N-oxide metabolite isolated from human liver microsomes and solubilized protein from *E. coli* transformed with pTrcHLFMO 3 (Table 2A, B).

The S-oxygenation of sulfur-containing substrates for the HLFMO 3 was investigated to provide a sensitive and direct method to study HLFMO (3) stereoselectivity. Determination of HLFMO 3 stereoselectivity could reveal information about enzyme mechanism as well as the incidence of competing achiral non-enzymatic oxidation processes (Cashman et al., *J. Amer. Chem. Soc.* 111:4844–4852 (1989); Cashman & Olsen, *Mol. Pharmacol.* 38:573–585 (1990)). Comparison of the stereoselectivity results obtained with human liver microsomes and recombinant HLFMO 3 with the results obtained using other FMO enzymes could also provide correlative information about enzyme substrate binding site topology. As shown in Table 3, 4-bromophenyl-1,3-oxathiolane was exclusively converted to (−)-trans-4-bromophenyl-1,3-oxathiolane S-oxide by both human liver microsomes and solubilized protein from *E. coli* transformed with pTrcHLFMO 3.

In contrast, (+)-4-bromophenyl-1,3-oxathiolane was converted to a mixture of cis and trans-4-bromophenyl-1,3-oxathiolane S-oxides by both human liver microsomes and cDNA expressed HLFMO 3. In fact, (+)-4-bromophenyl-1,3-oxathiolane is stereoselectively S-oxygenated to the trans S-oxide. In good agreement with previous studies employing hepatic preparations from animals (Cashman et al., *J. Amer. Chem. Soc.* 111:4844–4852 (1989); Cashman & Williams, *Mol. Pharmacol.* 37:333–339 (1990); Cashman et al., *Chem. Res. Toxicol.* 3:344–349 (1990)), the FMO monooxygenase preferentially attacks the sulfur atom at the least sterically hindered lone pair. The results suggest that FMO may be solely responsible for 4-bromophenyl-1,3-oxathiolane S-oxide formation though this does not rule out the involvement of cytochromes P-450. The stereoselective S-oxygenation of 2-methyl-1,3-benzodithiole was also investigated.

As shown in Table 4 human liver microsomes form mainly the (+)-(1R,2R)trans-S-oxide diastereomer although both cis diastereomeric S-oxides were formed, albeit in lower amounts. In contrast, expressed HLFMO 3 formed mainly the (+)-(1R,2S)cis S-oxide diastereomer although significant amounts of the other cis and (+)(1R,2R)trans S-oxide diastereomers were formed. In the presence of expressed HLFMO 3 or human liver microsomes no detectable amount of (−)-(1S,2R)trans-2-methyl-1,3-benzodithiole S-oxide was also formed (Table 4). Because the major product formed by expressed and highly purified pig liver FMO (form 1) is the cis-(−)-(1S,2R) S-oxide, it is likely that the major trans S-oxide product formed in human liver microsomes is catalyzed by cytochromes P-450.

Kinetic constants for the N- and S-oxygenation of various substrates in the presence of human liver microsomes or solubilized protein from *E. coli* transformed with pTrcHLFMO 3 were calculated from the rate of N- or S-oxide formation at variable substrate concentrations by the HPLC procedures described in the Experimental Procedures. The Km and Vmax values obtained from double reciprocal plots of velocity versus substrate concentration were listed in Table 5. As shown by the kinetic constants listed in Table 5, the values obtained for human liver microsomes were comparable to those obtained in the presence of cDNA-expressed HLFMO 3. The kinetic constants (Table 5) show that thiobenzamide, trifluoperazine, 10-(N,N-dimethylaminopentyl)-2-trifluoromethyl)phenothiazine (compound 5), and (+) and (−)-4-bromophenyl-1,3-oxathiolane are excellent substrates for the expressed HLFMO 3 and adult human liver microsomes. The concentration of substrate required to half-saturate the enzyme is in the general range reported previously for similar compounds. The turnover at infinite substrate concentration is similar to that reported by others for microsomal transformation with these same substrates (McManus et al., *Drug Metab. Dispos.* 15:256–261 (1987); Lemoine et al., *Arch. Biochem. Biophys.* 276:336–342 (1990)). In agreement with earlier work for other FMO's, HLFMO 3 does not catalyze S-oxidation of the phenothiazine tricyclic sulfur atom (Nagata, *Chem. Res. Toxicol.* 3:372–376 (1990)). This result is consistent with the mechanism proposed for animal FMOs which requires a "soft," highly polarizable nucleophilic atom as oxygenatable substrates.

That no detectable amount of trifluoperazine S-oxide or other 10-(N,N-dimethylalkyl)-2-trifluoromethyl) phenothiazine S-oxide were detected in preparations of proteins from pTrcHLFMO 3 transformed or non-transformed *E. coli* suggests that non-enzymatic or non-HLFMO 3 enzymic oxidations do not contribute to the determination of the kinetic constants listed in Table 5.

Dichloromethane extracts of metabolic incubations of selected reactions catalyzed by human liver microsomes and solubilized protein from transformed *E. coli* were purified by preparative HPLC and were subjected to mass spectral analyses. The mass spectral data of S-oxide metabolites was listed in Table 2 and was virtually identical to the data of the authentic material. Taken together, the data for N- and S-containing compounds clearly showed that HLFMO 3 cDNA expressed in *E. coli* and adult human liver microsomes catalyzed selective oxygenation of various tertiary-amine and nucleophilic sulfur-containing substrates.

TABLE 1

N- and S-Oxygenation of Various 10-(N,N-Dimethylaminoalkyl)-2-(Trifluoromethyl) Phenothiazines by Human Liver Microsomes and cDNA-Expressed Human Liver Flavin-Containing Monooxygenase[a]

| Substrate | Alkyl Side Chain | Human Liver Microsomes | | Expressed HFLMO | |
|---|---|---|---|---|---|
| | | N-oxide | S-oxide | N-oxide | S-oxide |
| | n | pmol/min/mg of protein | | pmol/min/mg of protein | |
| Chlorpromazine | 3 | 58.9 ± 7.4 | 29.3 ± 3.7 | 10.2 ± 1.2 | ND |
| Compound 2 | 2 | 27.8 ± 4.5 | ND[b] | 30.4 ± 6.8 | ND |
| Compound 3 | 3 | 149.9 ± 14.3 | 12.2 ± 3.3 | 53.2 ± 12.9 | ND |
| Compound 4 | 4 | 201.2 ± 18.8 | 31.0 ± 15.8 | 118.0 ± 7.8 | ND |
| Compound 5 | 5 | 252.1 ± 38.6 | 32.5 ± 33.7 | 200.0 ± 45.7 | ND |
| Compound 6[c] | 6 | — | — | — | — |

[a]Incubations were performed as described in Example 8 with 0.1 mM substrate. The values are the mean of 5 determinations ± SD.

[b]ND, not detectable, limit of detection 10 pmol/min/mg of protein.

[c]In a separate experiment, Compound 6 gave similar values to the values listed above for Compound 5.

TABLE 2A

Mass Spectral Properties of N- and S-Oxide Metabolites of cDNA-Expressed Human Liver Flavin-Containing Monooxygenase (form II)

| Metabolite | MW | CI[a] or LSIMS[b] | EIMS |
|---|---|---|---|
| | | m/z (relative intensity) | m/z (relative intensity) |
| 2-Methyl-1,3-benzodithiole S-oxide | 184 | 185[a] (100) 153 (19.8), 140 (100), 134 (29.4), 96 (40.5) | 184 (38.1), 166 (4.8), |
| (-)-4-Bromophenyl-1,3-oxathiolane[c] S-oxide | 260 | 253/261[a] (14.0/14.0), 183 (100) 206/204 (11.9/11.4), 185/183 (38.1/42.1, 57 (100) | 262/260 (13.2/13.2), 235/232 (15.9/15.9), |
| 10-(N,N-Dimethylaminopentyl-2-trifluoromethyl)-phenothiazine N-oxide | 396 | 381[a] (7.9), 292 (10.8), 258 (31.8), 57 (100) | NP[d] |
| Thiobenzamide S-oxide | 153 | 239[a] (100), 135 (4.3), 121 (10.1) | 238 (28.6), 135 (100) |

[a]CI, Chemical Ionization, carrier gas was ammonia resulting in protonated molecular ions.
[b]LSIMS, Cs+ liquid secondary ion mass spectrometry using a thioglycerol matrix.
[c]cis and trans diastereomers gave virtually identical spectra.
[d]NP, not possible, the metabolite was unstable to the mass spectrometry experiment.
[e]Under the conditions of the mass spectrometry experiment, the S-oxide dimerized to yield 3,5-diphenyl-1,2,4-thiadiazole (MW 238). This was confirmed by an independent synthesis and MS experiment of an authentic sample (Hanzlik and Cashman, J. Org. Chm. 47 4645–4650 (1982)).

TABLE 2B

Mass Spectral Properties of N- and S-Oxide Metabolites of Human Liver Microsomes

| Metabolite | MW | CI[a] or LSIMS[b] | EIMS |
|---|---|---|---|
| | | m/z (relative intensity) | m/z (relative intensity) |
| 2-Methyl-1,3-benzodithiole S-oxide | 184 | 185[a] (100) | 184 (11.9), 169 (6.3), 153 (19.8), 140 (71.4), 57 (100) |
| (-)-4-Bromophenyl-1,3-oxathiolane[c] S-oxide | 260 | 262/260[a] (55.7/55.7), 234/232 (60.4/56.4) | 262/260 (6.7/6.7), 234/232 (6.7/6.7), 186/184 (9.4/9.4), 184/182 (15.5/15.5), 57 (100) |
| 10-(N,N-Dimethylaminopentyl-2-trifluoromethyl)-phenothiazine N-oxide | 396 | 381[a] (37.3, 367 (28.6), 292 (11.1), 258 (46.0), 123 (100) | NP |
| Thiobenzamide S-oxide | 153 | 239[a] (23.0), 136 (29.8), 122 (71.2) 74 (100) | NP (87.5), 59 |

[a]CI, Chemical Ionization, carrier gas was ammonia resulting in protonated molecular ions.
[b]LSIMS, Cs+ liquid secondary ion mass spectrometry using a thioglycerol matrix.
[c]cis and trans diastereomers gave virtually identical spectra.

TABLE 2C

Mass Spectral Properties of N- and S-Oxides from Synthetic Sources

| Metabolite | MW | CI[a] or LSIMS[b] | EIMS |
|---|---|---|---|
| | | m/z (relative intensity) | m/z (relative intensity) |
| 2-Methyl-1,3-benzodithiole S-oxide | 184 | ND[f] | 184 (16), 162 (11.5), 151 (13.5), 153 (12), 140 (100) |
| (-)-4-Bromophenyl-1,3-oxathiolane S-oxide | 260 | ND | 262/260 (30.4/29.5), 234/232 (43.6/40.6), 165/183 (100/94.4) |
| 1'10-(N,N-Dimethylaminopentyl-2-trifluoromethyl)- | 396 | 382[b] (100), 359 (23.6), 341 (57.3) | 380 (42.9), 366 (10.5), 293 (4.4), 280 (9.1), |

TABLE 2C-continued

Mass Spectral Properties of N- and S-Oxides from Synthetic Sources

| Metabolite | MW | CI[a] or LSIMS[b] | EIMS |
|---|---|---|---|
| phenothiazine N-oxide | | | 267 (10.9, 266 (16.2), 248 (11.5), 100 (100) |
| Thiobenzamide S-oxide | 153 | ND | 238 (34.6), 135 (100), 103 (18.6) |

[a]CI, Chemical Ionization, carrier gas was ammonia resulting in protonated molecular ions.
[b]LSIMS, Cs+ liquid secondary ion mass spectrometry using a thioglycerol matrix.
[f]ND, not done.

TABLE 3

S-oxygenation of (+) and (-)-4-Bromophenyl-1,3-Oxathiolane by Adult Human Liver Microsomes and CDNA-Expressed Human Liver Flavin-Containing Monooxygenase[a]

| | Human Liver Microsomes | | Expressed HLFMO | |
|---|---|---|---|---|
| Substrate | cis S-oxide | trans S-oxide | cis S-oxide | trans S-oxide |
| | % (nmol/min/mg of protein) | | % (nmol/min/mg of protein) | |
| (+)-4-Bromophenyl-1,3-oxathiolane | 40.4 (5.3 ± 0.9) | 59.5 (7.8 ± 1.7) | 38.5 (0.5 ± 0.3) | 61.4 (0.8 ± 0.2) |
| (-)-4-Bromophenyl-1,3-oxathiolane | ND[b] | 100 (2.4 ± 0.9) | ND | 100 (0.7 ± 0.1) |

[a]Incubations were carried out as described in Example 8. The values are the mean of determinations ± SD.
[b]ND, not detectable, limit of detection 15 pmol/min/mg of protein.

TABLE 4

Stereoselective S-Oxygenation of 2-Methyl-1,3-Benzodithiole by Microsomes and cDNA-Expressed Flavin-Containing Monooxygenise from Human Liver[a]

| | S-Oxide Product Formed | | | |
|---|---|---|---|---|
| Enzyme Preparation | cis (+)-(1R,2S) | cis (-)-(1S,2R) | trans (+)-(1R,2R) | trans (-)-(1S,2R) |
| | % Diastereomer (amount formed, pmol/min/mg of protein) | | | |
| Human Liver Microsomes | 28.2 (176 ± 34) | 12.3 (77 ± 27) | 59.5 (372 ± 35) | ND[b] |
| Expressed FMO | 48.6 (54 ± 22) | 19.8 (22 ± 2) | 31.5 (35 ± 27) | ND |

[a]Incubations were carried out in the presence of a 0.5 mM NADPH generating system, 0.6 mM DETAPAC, 125 nmol substrate, potassium phosphate buffer (pH 8.4) and enzyme (0.75 mg microsomes or 1.4 mg expressed protein). Each value was determined by HPLC and was the mean of 5 determinations of ± SD.
[b]Not detectable, ND, limit of detection was 10 pmol/min/mg of protein.

TABLE 5

Kinetic Constants for Oxygenation of Tertiary Amines and Sulfur-Containing Compounds by Adult Human Liver Microsomes and cDNA-Expressed Human Liver Flavin-Containing Monooxygenase[a]

| | Human Liver Microsomes | | Expressed HLFMO | |
|---|---|---|---|---|
| Substrate | $K_m$ µM | $V_{max}$ (nmol/min/mg of protein) | $K_m$ µM | $V_{max}$ (nmol/min/mg of protein) |
| Thiobenzamide | 14.9 | 1.3 | 72.6 | 1.44 |
| Trifluoperazine | 92.7 | 0.253 | 139.0 | 0.204 |
| Compound 5 | 6.8 | 0.098 | 64.6 | 0.023 |
| (+)-4-Bromophenyl[b]-1,3-oxathiolane | 50.0 | 2.87 | 142.3 | 0.180 |

TABLE 5-continued

Kinetic Constants for Oxygenation of Tertiary Amines and Sulfur-Containing Compounds by Adult Human Liver Microsomes and cDNA-Expressed Human Liver Flavin-Containing Monooxygenase[a]

| | Human Liver Microsomes | | Expressed HLFMO | |
|---|---|---|---|---|
| Substrate | $K_m$ $\mu M$ | $V_{max}$ (nmol/min/mg of protein) | $K_m$ $\mu M$ | $V_{max}$ (nmol/min/mg of protein) |
| (-)-4-Bromophenyl[b]-1,3-oxathiolane | 166.0 | 5.2 | 310.8 | 2.94 |

[a]The kinetic constants were calculated from initial velocity measurements by the HPLC procedure described in Example 8 and the data was analyzed using Kinet Asyst. The enzyme preparations were different from those used elsewhere in this study and may account for the differences in values obtained.
[b]Formation of the trans S-oxide.

Screening

Adult human liver microsomes catalyze the NADPH-dependent N-oxygenation of 10-(N-n-aminooctyl)-2-(trifluromethyl)phenothiazine to the corresponding oximes through the intermediacy of the hydroxylamine. In the presence of adult human liver microsomes, the primary amine is stereoslectively converted to the cis oxime but addition of the alternative competitive substrate hydroxylamine hydrochloride apparently decreases the amount of aliphatic hydroxyl amine retroreduction because an increase in oxime formation was observed. In the presence of hydroxylamine hydrochloride, however, the product recovered was formed with very low stereoselectivity. Studies on the biochemical mechanism of oxime formation suggest that cis-oxime formation was largely dependent on the human flavin-containing monooxygenase (form 3). This conclusion is based on the effects of incubation conditions on product formation and product stereoselectivity. The retroreduction of intermediate hydroxylamine was dependent on NADPH but not catalyzed by human flavin-containing monooxygenase (form 3) or any one of seven prominent cytochromes P-450 that have been well-characterized in the human liver microsomes examined. The results suggest that aliphatic primary amines are efficiently sequentially N-oxygenated in the presence of human liver microsomes to hydroxylamines and then to oximes mainly by the human flavin-containing monooxygenase. Retroreduction of intermediate hydroxylamine is apparently facilitated by a novel but as yet poorly characterized enzyme system that does not employ any of the currently known well-characterized cytochrome P-450 enzymes present in adult human liver microsomes.

Thus, in vitro FMO can be used to screen a wide variety of chemicals, drugs, agrichemicals or biological materials for novel biological or pharmacological activities. For example, chemicals that contain tertiary amines or sulfur atoms are converted to their corresponding tertiary amine N-oxides or sulfoxides. In vivo, these metabolites are biologically active in their own right or serve as reservoirs of parent drug (after reduction in vivo to the parent drug). For example, sulindac is a widely used anti-inflammatory agent which is sold as the S-oxide prodrug (Brogden et al., *Drugs* 16:97–114 (1978)). When it is administered to humans, it is reduced to the sulfide which is the active anti-inflammatory agent. The oxidation-reduction of the antiinflammatory agent sulindac occurs, according to the following:

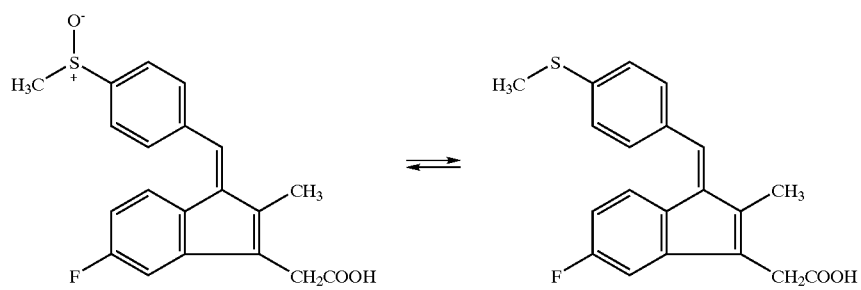

Presumably, the oxidation-reduction cycling in vivo provides a reservoir of active drug in equilibrium with the S-oxide metabolite of the parent drug. This dynamic equilibrium is important in drug targeting because sulfoxides tend to stay inside cells and accumulate due to the polar nature or are kept out of cells and are excreted out of the body. Screening drugs for their potential human metabolism to polar S-, N-, or P-oxides is a (bio) indicator of the type and extent of metabolism, distribution or elimination of the drug/chemical in the body. Screening drug candidates with recombinant HLFMO (form 3) economizes on the use of animals in research and is more directly applicable to human drug metabolism.

Screening drugs as substrates for FMO is also useful in drug design. For example, cimetidine is metabolized largely to a single metabolite, cimetidine S-oxide in adult humans. Recent studies have pointed to the involvement of FMO (form 3) in the formation of the S-oxide metabolite. The determination of the FMO substrate specificity of other anti-ulcer agents indicates whether the anti-ulcer agent is sulfoxidized in a similar fashion. Others have shown that active anti-ulcer drugs are substrates for FMO (Ziegler, *Drug Metab. Reviews* 19:1–32 (1988)). It is possible that flavin-containing monooxygenase has the same structural requirements (substrate specificity) that the $H_2$-receptor possesses. Screening the anti-ulcer candidate drug against cDNA-expressed FMO form 3 indicates whether a candidate is an effective anti-ulcer agent in vivo. The use of predictive strategies can save enormous amounts of money usually devoted to pharmacological evaluation in animals or non-human primates.

Screening Methods

Screening drugs, chemicals, agrichemicals or biologicals for FMO activity as substrates can be readily done by one of three methods:

1. One method is to incubate the cDNA-expressed enzyme and substrate in the appropriate buffer and follow the amount of oxygen consumed with an oxygen electrode. Because FMO is a monooxygenase, one molecule of oxygen is consumed for in every molecule of substrate oxidized (Ziegler and Mitchell, *Arch. Biochem. Biophys.* 150:116–125 (1972)). Quantification of oxygen consumed indicates the efficiency of N-, S- or P-oxygenation by HLFMO 3.

2. A second method to assay for FMO activity is to monitor the amount of NADPH consumed (and formation of NADP$^+$) spectrophotometrically using a UV-vis spectrometer. One molecule of NADPH is consumed for every molecule of substrate that is oxidized (for an example of pesticide screening, see (Hajjar and Hodgson, *Science* 209:1134–1136 (1980)).

3. A third method is an HPLC procedure to separate the parent chemical from the oxygenated metabolite for example, see Cashman and Proudfoot, *Anal. Biochem.* 175:274–280 (1988)).

The screening of chemicals for FMO substrate activity can be utilized for biologicals, rare chemicals (or precious chemicals), agricultural agents (i.e., herbicides, pesticides and fungicides). Screening of chemicals, drugs, agrichemicals and biologicals for FMO activity reveals novel biologically active chemicals using a novel mechanism of action or unusual selectivity. An example from the agrichemical literature is described in Schuphan et al., *Science* 205:1013–1015 (1979) and Park et al., *Chem. Res. Toxicol.* 5:193–201 (1992).

FMO as a Liver Cancer Diagnostic

One potential application of the difference between fetal human liver FMO (form 1) and adult human liver FMO (form 3) is that the presence of significant amounts of form 1 FMO in the adult human liver indicates a cancerous condition.

Generally, stem cells are programmed to undergo specific developmental changes and produce specific proteins at each stage in cellular maturation. Sometimes (for unknown reasons) the stem cells makes an error and undergoes steps leading to development of a cancerous cell. Sometimes, embryonic proteins or cells are found in the cancerous tissue (Alberts et al., in "Molecular Biology of the Cell" pp. 611–621 Garland Publishing, NY (1983)). The fetal human liver FMO form 1) should not be present in the adult human liver because it is a fetal or embryonic protein. If it is detected, this would indicate a dysfunctional adult human liver. To detect the fetal human liver FMO (form 1) selective hybridization protocols involving specific form 1 FMO oligonucleotides that are not recognized by form 3 FMO could be developed This would offer an "early warning" diagnostic of adult human liver cancer.

Amine Biochemistry and Biosynthesis of Rare Chemicals

Employing enzyme-immobilized fluidized reactors, adult human liver FMO (Form 3) can be employed to metabolize primary amines to hydroxylamines. This is of practical utility as a biocatalyst to selectively transform primary amines (or secondary and tertiary amines) to their oxidized products. This is useful for synthesis of precious or rare chemicals. Some of the oxidation products (i.e., tertiary amine N-oxides from tertiary amines or nitrones from oxidation of secondary hydroxylamines) are not indefinitely stable and decompose or rearrange to other products. This also is useful from a synthetic standpoint to prepare specific functional groups from amine-containing starting materials. Biosynthesis of specific amine oxidation products are also useful in the general area of producing prodrugs or elaborating pro-toxin chemistry. The properties of oxidation products of amines thus are useful in chemical synthesis, drug design or a variety of chemi-enzymatic procedures that involve amines, hydroxylamines, secondary amines or tertiary amines. An example of some applications of using N-oxides as precursors or metabolites of amines in the tertiary amine field can be found in J. R. Cashman in "Progress in Pharmacology land Clinical Pharmacology," Vol. 8, pp. 117–126, edited by P. Hlavica and L. A. Damani, N.Y. Enstav Fischer Verlag (1991).

Mercapturates as Biomarkers

In humans, electrophilic chemicals, biologicals, and agrichemicals are conjugated with glutathione. The glutathione conjugate is further processed to the mercapturate which is the N-acetylcysteine conjugate (Park et al., *Chem. Res. Toxicol.* 5:193–201 (1992)). Thus, 1,3-dichloropropene, a widely used fungicide is converted to its cysteine S-conjugate in vitro and to its mercapturate in vivo. The mercapturate is a biomarker for fungicide exposure to humans.

Mercapturates and S-cysteine conjugates of chemicals, drugs, and biologicals are substrates for FMO from animals and humans. The S-oxide products are not indefinitely stable and, depending on the functional groups present, eliminate or rearrange to other products. The by-products are selective biomarkers for the S-oxygenation of chemicals by FMO. For example, a S-cysteine conjugate of an isoprene moiety (farnesylcysteine methyl ester) is an excellent substrate for FMO. The S-oxide is not stable and the farnesyl group is cleaved. Because farnesylation of ras proteins is required for oncogene products, FMO-mediated S-oxidation of farnesylated proteins may be protective against cancer. Further, by-products of the S-oxidation of farnesylated ras proteins could be useful bioindicators of protection against cancer.

Diallate: A Novel Pro-herbicide

Diallate is an herbicide that undergoes a novel type of S-oxidative bioactivation to a more potent herbicide, according to the following reaction scheme:

Diallate

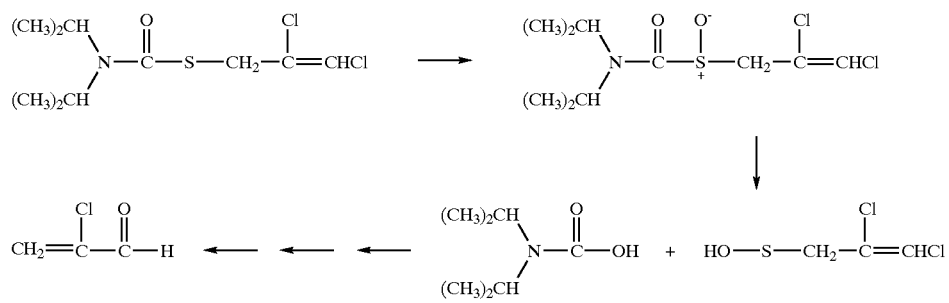

Diallate is a pro-herbicide that is S-oxidized. Further reactions ensue to produce the active compound. A screen is set up to evaluate FMO-mediated S-oxidation coupled with herbicidal activity assay. Novel metabolism and pro-herbicide screening are undertaken to indicate active agrichemicals.

Anti-depressants: Utility of FMO Drug Screening Product

Many anti-depressant drugs of the phenothiazine class possess a tertiary amine side chain that is required for pharmacological activity (i.e., chlorpromazine). The N-oxygenation product of chlorpromazine is shown by the following formula:

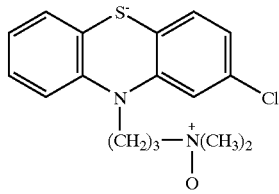

Other central nervous system drugs, like the antipsychotic trifluoperazine, is similar in structure but has a cyclic tertiary amine side chain. There is apparently a specific structure activity relationship for N-oxygenation of the side chain by adult human liver FMO (form 3) (see Table 1).

Screening of chemicals for FMO activity may indicate drugs with superior pharmacological activity, disposition profiles or better pharmacokinetic properties. Screening drugs for FMO N-oxygenation activity provides insight into more optimal drug design/metabolism properties.

N-Oxide Rearrangements

Tertiary amines are N-oxygenated in adult human liver preparations containing FMO activity to tertiary amine N-oxides. Some of the tertiary amine N-oxides are not stable and undergo Cope-type elimination to produce unusual and possibly unanticipated metabolites. An example is from the antiarrhythmic drug verapamil which undergoes N-oxygenation and Cope-type elimination to produce styrene. Cope-type elimination of verapamil N-oxide (compound 7) to the hydroxylamine (compound 8) and styrene (compound 9) has been observed (Cashman et al., Mol. Pharmacol. 36:497–503 (1989)), according to the following reaction scheme:

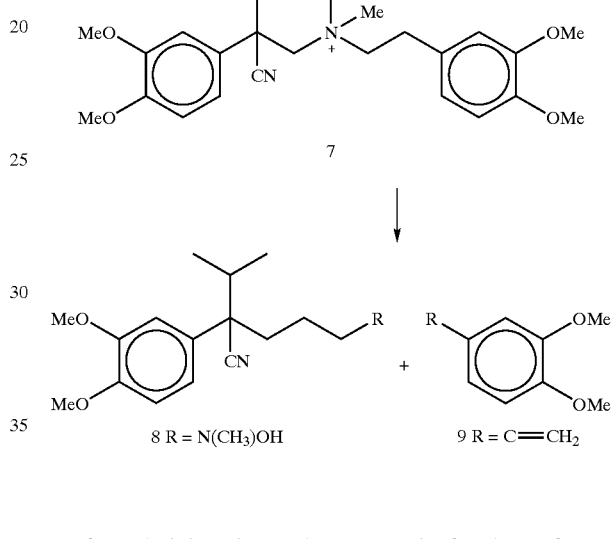

After administration to humans, 2% of a dose of verapamil is recovered unchanged. However, only 50% of a dose is accounted for in terms of identifiable metabolites. Verapamil is metabolized to the N-oxide which undergoes Cope-type elimination to produce novel metabolites. Screening with cDNA-expressed HLFMO obviates whether this is the case and whether the metabolite produced (i.e., styrene) is responsible for some of the toxicities associated with administration of verapamil. This is another example of the usefulness of HLFMO 3 in drug design.

Asymmetric Chemi-Enzyme Synthesis

Synthesis of precious or rare chemicals (especially with centers of chirality) will be performed often in the future. HLFMO 3 provides a convenient way to do this (even on a large scale using enzyme-immobilized fluidized reactors). For example, (−)-4-bromophenyl-1,3-oxathiolane is selectively oxygenated to only one S-oxide diastereomer. The reaction of an electrophilic alkyl halide (RX) with the carbanion of the 4-bromphenyl-1,3-oxathiolane S-oxide (see Table 3), to provide diastereomeric derivatives for further asymmetric chemical studies according to the following reaction scheme.

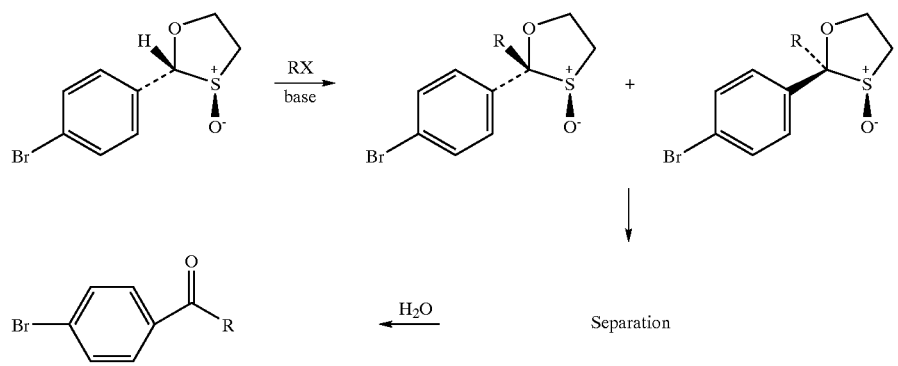

If R is a material with a center of chirality or even a prochiral center, by using this simple chiral auxiliary (i.e., S-oxide) in a chemical reaction one can achieve asymmetric induction and synthesis of a rare chemical. This is not limited to this particular system, and this scheme just provides an example. This is shown using 4-bromophenyl-1,3-oxathiolane as the starting material because sulfoxidation has been previously shown (see Table 3).

In Vivo Folding Catalyzed by HFMO 3

Expression of proteins and peptides in *E. coli* has been shown in some cases to be limited by the periplasmic folding process. In the process, most of the expressed peptide or protein is correctly transported and the signal peptide is cleared off, but only a certain fraction of the expressed material achieves a native state. Sometimes, this fraction of native protein is dependent on the growth conditions of the cell (Skerra and Pluckthun, *Protein Eng.* 4:971–979 (1991)). HLFMO 3 is an ideal in vivo disulfide-forming and folding catalyst to assist the renaturation of proteins in bacterial or other expression vectors. It is a simple experiment to co-transfect (or genetically link) the HLFMO 3 cDNA in an appropriate expression system, a plasmid containing HLFMO 3 and the gene encoding the protein of interest. Because different recombinant proteins and peptides have different rate-limiting steps in their folding, co-expression with HLFMO 3 provides a way to get around many problems associated with recombinant protein or peptide expression. Providing an endogenous disulfide catalyst to facilitate protein folding in vivo provides an efficient means of increasing the yields and the fidelity of expressed recombinant peptides and proteins.

Expression of FMO Fusion Proteins

Generally, expression in *E. coli* of fusion proteins is more efficient than expression of the same protein without extra amino acids. This is the case for FMO, although it is not due to protein degradation, proteolysis or other instabilities. As a model system for HLFMO 3, it was observed that a 34 amino acid N-terminal β-galactosidase fusion protein of pig liver FMO expressed in *E. coli* was more stable and expressed at a higher level than when the 34 amino acid segment was not present. This is probably also the case for the expression of the adult human liver (form 3). Briefly, the vector SK containing most of the pig liver FMO (form 1) cDNA was ligated to a restriction site that had an open reading frame encoding part of the β-galactosidase gene. The vector was used to transform *E. coli* cells. The production of the fusion protein was checked on SDS-PAGE and positively confirmed by Western blotting with a specific antibody directed against pig liver FMO (form 1). FMO enzyme activity was apparent by HPLC analysis of organic extracts (as described in Example 8). The conclusion was that greater levels of enzyme with significant activity could be obtained by employing a fusion protein approach to the expression of FMO. It was concluded that the same would be true for HLFMO (form 3).

Stable FMO Transfer

Transfection with form 1 FMO cDNA gives a cell model with a very different profile of FMO-mediated metabolites than transfection with form 3 FMO cDNA. For example, the substrate specificity of adult human liver FMO (form 3) is very different than form 1 FMO. The ability to transfect with either FMO provides a convenient cell model for adult vs. fetal human liver FMO studies.

If for example, procarcinogenic aromatic amines were selectively bioactivated by form 3 and not form 1 FMO, this provides a means to specifically evaluate the biological consequences of FMO-mediated procarcinogen bioactivation in a cell. Currently, this is not possible because of the instability of human cells possessing FMO activity and because of the possible complications of other monooxygenases.

CVI (monkey fibroblast) and Hep G2 (human hepatocyte) cells have been transfected with pig liver FMO (form 1) cDNA using a lipofection technique. The recombinant plasmid system that was used contained a pSVK3 promoter and a pig liver FMO cDNA insert. In a separate control experiment, a luciferase gene was transfected as a control. The CV1 and Hep G2 lipofection showed some apparent cell toxicity problems. An ultrasensitive HPLC assay detected FMO-mediated N-oxygenase activity. In parallel, cells transfected with the luciferase gene showed good luciferase activity. This gives a tool to study cellular consequences of FMO action in a defined, highly reproducible system. Adult human liver FMO (form 3) follows a similar procedure as was used for pig liver FMO transfection. A gene which codes for an enzyme that forms a fluorescent marker product such as chloramphenicol acetyl transferase is cotransfected with the adult human liver FMO (form 3) cDNA (Young et al., *Analyt. Biochem.* 197:401–407 (1991)). The marker enzyme is constructed to be readily removed after expression and detection of FMO (form 3).

The following examples are presented to illustrate the present invention and to assist one of ordinary skill in the art in making and using the same. The examples are not intended in any way to otherwise limit the scope of the invention.

EXAMPLE 1

Isolation of cDNA Clones for Adult Human Liver FMO

Human adult liver was obtained and RNA was extracted by the acid guanidium thiocyanate/phenol/chloroform method (Chomczynski & Sacchi, *Anal. Biochem.* 162, 156–159 (1987)). Poly(A)+ RNA was purified by chromatography with oligo (dT)-cellulose (Aviv & Leder, *Proc. Natl. Acad. Sci. USA* 68:1408–1412 (1972)). The genomic DNA was isolated according to a standard protocol (Gross-Bellard et al., *Eur. J. Biochem.* 26, 32–38 (1973)).

The adult human liver λ-gt11 cDNA library was obtained from Clontech (Mt. View, Calif.) and the adult human liver λ-gt11 library was constructed by standard procedures (Huynh et al., DNA Cloning: A Practical Approach (IRL, Oxford, U.K.), 49–78 (1985)). The cDNA libraries were screened by an in situ hybridization technique (Benton & Davis, *Science* 316:180–182 (1987)) at a density of 100,000 pfu/132-mm-diameter plate. Approximately 2×10$^6$ plaques were examined. The probe used was a mixture of three oligonucleotides complementary to the pig liver FMO (PLFM0) cDNA (Gasser et al., *Biochemistry* 29: 119–124 (1990)). The three 36-mer oligonucleotide probes were prepared by the UCSF Biomolecular Resource Center with an Applied Biosystems Model 380B DNA synthesizer using phosphoramidite chemistry. PLFM01, a 36-mer of sequence 5'-ATCGCTCCTCTCAAAGCAGGTGGGCTCCAGC CTTC-3' (SEQ ID No. 14), is complementary to the pig liver cDNA nucleotide sequence 127–162, PLFM02 a 36-mer of sequence 5'-CTCATCAAGGGGAAAGCAAAGGTGTATCCAGT-3' (SEQ ID No. 1), is complementary to the pig liver cDNA nucleotide sequence 1041–1076 and PLFM03, a 36-mer of sequence 5'-GAATGTTCGGTCCCACTGGGTCATGATGATAG CATTCCT-3' (SEQ ID No. 2), is complementary to the pig liver cDNA nucleotide sequence 1509–1545. Purified oligonucleotides were 5'-end-labeled with [gamma-$^{32}$P]ATP and T4 polynucleotide kinase. Filters from the first screening were prewashed in 50 mM Tris HCl (pH 8.0), 1M NaCl, 1 mM EDTA, and 0.1% SDS for 2 h at 42° C. Prehybridization was carried out in 6×SSC, 0.5% N-lauroyl sarcosine, 10×Denhardt's solution and 50 mg/ml of denatured salmon sperm DNA for 4 h at 45° C. The $^{32}$P-labeled probes (10$^6$ cpm/filter) were added to the same prehybridization buffer without N-lauroyl sarcosine and hybridization was carried out for 16 h at 45° C. The filters were washed five times in 2×SSC containing 0.1% SDS for 10 min at room temperature, twice for 1 h at 55° C., dried and exposed to Kodak X-Omat AR5 films at −80° C. for 24 h with intensifying screens. The positive clones were further purified by additional screenings under the same hybridization conditions.

EXAMPLE 2

Preparation of Phage DNA, Subcloning, and Restriction Endonuclease Mapping

Phage stocks of the positive clones were prepared and the cDNA EcoRI inserts were isolated. The various EcoRI fragments were subcloned into Bluescript II vectors using competent *E. coli* XL1-Blue and NM 522 cells. A restriction endonuclease map was obtained by digestion with appropriate restriction enzymes.

EXAMPLE 3

Nucleotide Sequence Analysis

The nucleotide fragments generated by treatment with EcoRI and other restriction endonucleases were subcloned into Bluescript (KS$^{+-}$ and SR$^{+-}$) vectors using competent *E. coli* NM 522 and XL1-Blue cells. For sequencing, the directed deletion strategy (Henikoff, *Gene* 28:351–359 (1984)) was used to obtain convenient sizes. Both strands of the double-stranded DNA clone were prepared and completely sequenced by the dideoxy method (Sanger et al., *Proc. Natl. Acad. Sci. USA* 74: 5463–5467 (1977)). Nucleotide sequences were compiled by the Eugene program (UCSF Socrates). Alignments were performed using an automatic shotgun program.

EXAMPLE 4

RNA Blot Analysis

Formamide-denatured poly(A)+ RNAs were fractionated by electrophoresis on a 1% agarose gel containing formaldehyde, transferred to nylon membranes, prehybridized for 4 h at 42° C., and hybridized with the nick-translated 5' [α-$^{32}$P]dATP cDNA insert (Rigby et al., *J. Mol. Biol.* 113: 237–251 (1977)) for 16 h at 42° C. The nylon membrane was washed under strong stringency conditions with five changes of 1×SSC, 0% SDS for 5 min each at room temperature and then washed twice with 0.1×SSC containing 0% SDS for 1 h at 65° C. The blots were dried and autoradiographed at −80° C. using an intensifying screen and Kodak X-Omat film.

EXAMPLE 5

Southern Blot Analysis

Samples of restriction endonuclease-digested genomic-DNA were fractionated by electrophoresis on a 0.8% agarose gel, transferred to a nylon membrane, and prehybridized in 50% formamide containing 5×SSC, 10×Denhardt's, 50 mg/ml salmon sperm DNA and 20 mM Na$_2$HPO4 (pH 7) for 4 h at 42° C. The $^{32}$P-labeled probe (10$^6$ cpm/ml) was added to the same prehybridization buffer and hybridization was carried out for 16 h at 42° C. The filter was washed five times with 2×SSC containing 0.1% SDS for 10 min at room temperature, twice with 1×SSC containing 0.1% SDS for 1 h at 65° C., dried and then visualized by autoradiography.

EXAMPLE 6

Extension of the 5' and the 3' Ends of HLFMO 3 cDNA Coding Strand

To obtain the full-length open reading frame for HLFMO 3 containing convenient ends for subcloning into the expression vector pTrc99A, the PCR technique was employed. For the PCR reaction, two oligonucleotide primers were designed. Primer A (5'-GGTACCACATGTCCATGGGGAAGAAAG-3' (SEQ ID No. 3) consisted of an AflIII site at the 5'-end of the HLFMO 3 cDNA. Primer B (5'-GACGTCGACGGATCCTTAGTGTCAACACA-3' (SEQ ID No. 4) had a SalI site at the 5'-end and a 13 nucleotide sequence complementary to the 3'-end of the HLFMO-'3 cDNA coding strand. The primers were synthesized with a Biosearch 8600 DNA synthesizer (Applied Biosystems, Foster City, Calif.) using phosphoramidite chemistry and purified on oligonucleotide purification cartridges (Applied Biosystems, Foster City, Calif.). The PCR was carried out with a Perkin-Elmer Cetus (San Jose, Calif.) DNA thermal cycler, using a GeneAmp DNA amplification reagent kit with the largest HLFMO3 cDNA clone from λ-gt11 as a template. Thirty thermal cycles were performed, and each cycle included a denaturation step at 98° C. for 1 sec, an annealing step at 50° C. for 15 sec, and an extension step at 60° C. for 4 min. After 30 cycles of PCR reaction, a full-length HLFMO 3 cDNA coding strand was obtained with AflIII restriction site and a SalI site attached to the 5'- and 3'-ends of the cDNA, respectively. The entire PCR insert was sequenced. The 5' and 3'-ends were also sequenced.

EXAMPLE 7

Prokaryotic Expression of HLFMO 3

After the PCR product was purified and digested with AflIII and SalI restriction enzymes, the generated fragment was subjected to fractionation by electrophoresis on 1% agarose gel, purified and subcloned into the NcoI-SalI sites of the inducible prokaryotic expression vector pTrc99A. The pTrc99A vector contained the lacZ ribosome-binding site and was driven by the strong hybrid trp/lac promoter (i.e., pTrc) under the control of the lacI$^q$allele of the lac repressor gene. The recombinant clones were identified by screening with a $^{32}$P labeled human FMO3 cDNA probe (Rigby et al., *J. Mol. Biol.* 113:237–251 (1977)) using the AflIII-SalI generated PCR fragment, and the correct insertion was confirmed by digestion with NcoI and SalI and DNA sequence analysis.

Competent NM522 *Escherichia coli* cells were transformed with the pTrc HLFMO 3 plasmid. Expression was performed in a modified MOPS medium (Craig et al., *Proc. Natl. Acad. Sci. USA* 88:2500–2504 (1991)) supplied with 20 mg/l FAD. After inoculation with a fresh overnight culture of NM522 containing pTrcHLFMO 3, the culture was grown at 37° C. until $Abs_{600}$ was approximately 0.5 absorbance units. Finally, IPTG (0.8 mM) was added to the culture to induce expression of protein and the culture was left to grow overnight at 37° C.

The bacterial pellet was resuspended in 5 volumes of 50 mM potassium phosphate buffer (pH 8.4) containing 1% Triton X-100, 0.1% L-, α-phosphatidylcholine (L-α-lecithin) from egg yolk, 500 μM PMSF, and 1 mM EDTA. The mixture was sonicated and then centrifuged to remove cellular debris. As a control, bacterial lysate extracts from IPTG-induced pTrc99A-transformed NM522 cells (i.e., pTrc99A without the HLFMO 3 cDNA insert) were prepared under the same conditions.

Total or solubilized proteins precipitated by PEG were fractionated by electrophoresis on 12% SDS PAGE (Laemmli, *Nature* 227:680–685 (1970)), transferred to nitrocellulose, and immunostained according to the procedure described previously (Towbin et al., *Proc. Natl. Acad. Sci. USA* 76:4350–4360 (1970). An antibody directed against the is guinea pig liver FMO (form 3) was used at a 1/1000 dilution and was a gift from Drs. K. Oguri and H. Yamada (Kyushi University, Fukuoda, Japan). An antibody directed against pig liver FMO form 1 was used at a 1/300 dilution and was a gift of Professor D. M. Ziegler (University of Texas, Austin, Tex.).

EXAMPLE 8

Enzyme Preparations and Incubations

Human liver samples were obtained from the Department of Surgery (UCSF) and with a protocol from the Medical College of Wisconsin (S. Wrighton). Pig and adult human liver microsomes were isolated as described before (Cashman, *Analyt. Biochem.* 160:294–300 (1987). Human liver FMO form 3 cDNA was expressed in competent NM522 *E. coli* cells after transformation with the pTrc HLFMO 3 plasmid. After sonication with a Branson model 125 sonicator (10 intervals of 5 sec, 6 power output level), the crude mixture was centrifuged to remove cell debris. The solubilized protein from the bacterial lysate was used directly for assay. Protein concentration was determined by the BCA protein assay from Pierce (Rockford, Ill.).

A typical incubation mixture (final volume 0.25 ml) contained hepatic microsomes (0.4 mg of protein) or bacterial lysate (2.3 mg of protein), NADP$^+$ (0.5 mM), glucose-6-phosphate (2.0 mM), glucose-6-phosphate dehydrogenase (1 IU), DETAPAC (0.8 mM) and potassium phosphate buffer (50 mM, pH 8.4). Reactions were initiated by the addition of substrate and terminated at designated times by the addition of three volumes of cold dichloromethane, mixed thoroughly and centrifuged to separate the aqueous and organic fractions. N- and S-oxide metabolic products in the resulting organic extracts were separated and quantified by HPLC. Chromatography was done on an IBM 9633 system with UV detection, fitted with a 5 μm AXXIOM (Richard Scientific, Novato, Calif.) silica phase column (4.5 μm×25 cm) with a mobile phase of isopropanol/methanol/60% perchloric acid (30:70:02, v/v) as previously described (Cashman & Yang, *J. Chromatog.* 532:405–410 (1990)). The HPLC system efficiently separated chlorpromazine, chlorpromazine N-oxide, and chlorpromazine S-oxide, which had retention volumes of 5.7, 6.2, 6.9, and 11.3 ml, respectively. In addition, with a mobile phase of methanol/acetonitrile/60% perchloric acid (80:20:0.08, v/v) the HPLC system efficiently separated trifluoperazine N-oxide, trifluoperazine, trifluoperazine N,S-dioxide, and trifluoperazine S-oxide which had retention volumes of 14.1, 15.9, 26.11, and 31.7 ml, respectively. Thiobenzamide and thiobenzamide S-oxide were quantified with this same, HPLC system employing a mobile phase of methanol/acetonitrile/60% perchloric acid (20:80:0.016, v/v) which gave retention volumes of 2.7 and 7.0 ml, respectively. The recovery of material as judged by HPLC was ≧95%, and 98% of the recovered metabolite was as the sulfoxides or as the tertiary amine N-oxides. The major metabolites formed in the incubations were also subjected to mass spectral analysis after extraction of isolated HPLC fractions.

The cis- and trans-diastereomeric S-oxides of (+) and (−)-4-bromophenyl-1,3-oxathiolane were separated and quantified by HPLC as previously described (Cashman et al., *J. Amer. Chem. Soc.* 112, 3191–3195 (1990)). RPLC of the S-oxide diastereomers with a Chiracel OT chiral analytical column (25 cm×0.15 cm inner diameter, Daicel Chemical Co., New York, N.Y.) was accomplished with a Beckman system, Kratos UV detector (240 nm) and a Hewlett Packard Integrator. The mobile phase consisted of methanol/isopropyl alcohol/hexane (1:10:89, v/v) which efficiently separated (+)-4-bromophenyl-1,3-oxathiolane, (+)-trans-4-bromophenyl-1,3-oxathiolane S-oxide, and (+)-cis-4-bromophenyl-1,3-oxathiolane S-oxide which had retention volumes of 5.4, 10.5, and 18.8 ml, respectively. The system also efficiently separated (−)-4-bromophenyl-1,3-oxathiolane, (−)-trans-4-bromophenyl-1,3-oxathiolane S-oxide, and (−)-cis-4-bromophenyl-1,3-oxathiolane S-oxide which had retention volumes of 5.4, 9.6 and 11.8 ml, respectively. Quantification was accomplished by comparing integrated HPLC peak areas after taking into account the difference in the extinction coefficients at 240 nm. Likewise, the cis and trans S-oxide diasteromers of (+)- and (−)-2-methyl-1,-benzodithiole were separated with a Chiracel OT chiral analytical column. The mobile phase consisted of methanol/isopropyl alcohol/hexane (0.25:2.8:7.25, v/v) which efficiently separated 2-methyl-1,3-benzodithiole and the (+)-(1R,2S), (−)-(1S,2R), (+)-(1R,2R), and (−)-(1S,2S) S-oxide diasteromers which had retention volumes of 17.6, 19.4, 23.6, and 24.5 ml, respectively.

The (N,N-Dimethylaminoalkyl)-2-trifluoromethyl) phenothiazines were separated on a IBM 9533 HPLC system with UV detection fitted with a 5 $\mu$m AXXIOM (Richard Scientific, Novato, Calif.) silica phase column (4.5 $\mu$m 25 cm) with a mobile phase of isopropanol/methanol 60% perchloric acid (30:70:0.2, v:v) as previously described (Cashman & Yang, J. Chromatog. 532, 405–410 (1990). The HPLC system efficiently separated the tertiary amine, the alkyl side chain tertiary amine N-oxide and the sulfoxide. In all cases examined, the substrate, N- or S-oxide metabolite or other metabolites were recovered in $\geq$85% efficiency and the substrate and N- or S-oxide accounted for a $\geq$95% of the material present.

disulfide bond forming catalyst in vitro to catalyze the renaturation of proteins by facilitating disulfide bond formation and protein folding. A typical reaction involves producing a steady state low level concentration of a chemical disulfide (i.e., cystamine or other thiols) by the monooxygenase and allowing disulfide exchange reactions to proceed to provide the correctly folded protein or peptide possessing the correct disulfide bonds.

The renaturation of proteins or peptides involves the following steps. In step 1, cysteamine is oxidized by HLFMO 3 to the disulfide. In step 2, the disulfide undergoes disulfide exchange with a cysteine of the protein. In step 3, another cysteine on the protein (or peptide) undergoes intramolecular disulfide bond formation to produce the native protein (or peptide) and regenerate cysteamine. The above steps are shown according to the following reaction scheme:

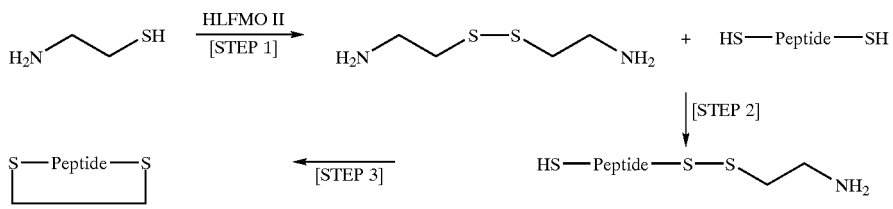

EXAMPLE 9

Purification of cDNA-Expressed Adult Human Liver FMO (Form 3)

The solubilized proteins from Example 7 are precipitated by the addition of PEG (8,000) to achieve a concentration of 6% (w/v) with constant stirring. The precipitate is collected by centrifugation at 100,000×g for 30 min. and discarded. To the supernatant is added PEG (8,000) until the mixture achieves a concentration of 14% (w/v). The precipitate that is collected by centrifugation at 100,000×g for 80 min. is resuspended in buffer I (10 mM potassium phosphate, pH 7.6, 1 mM EDTA, 0.5% Triton X-100), and the protein solution is applied to a DEAE-Sephacacel column that has previously been equilibrated with buffer I. After washing with buffer I, the cDNA-expressed adult human liver FMO (form 3) is eluted with buffer II (50 mM potassium phosphate, pH 7.6, 1 mM EDTA, and 0.5% Triton X-100). Fractions containing chlorpromazine N-oxygenation activity and anti-guinea pig liver FMO immunoreactivity are pooled, dialyzed against 10 mM potassium phosphate, pH 7.6, finally concentrated to achieve 0.5 mg of protein/ml by ultrafiltration using an Amicon apparatus and YM-30 membrane. The protein solution is loaded onto a hydroxylapatite column that was previously equilibrated with buffer I, and the cDNA-expressed adult human liver FMO (form 3) is eluted with a linear gradient of KCl in buffer I (0.1 M KCl, pH 7.6). Active fractions are collected (i.e. those fractions," exhibiting chlorpromazine N-oxygenation activity and anti-guinea pig liver FMO immunoreactivity), combined and concentrated as described above.

EXAMPLE 10

Refolding Peptides and Proteins with Adult Human Liver FMO (form 3)

The purified cDNA-expressed adult human liver (form 3), (or even a semi-purified preparation) can be used as a A typical incubation mixture (final volume, 0.25 mL) contains (0.5 mg of protein), NADP$^+$ (0.5 mM), glucose-6-phosphate (2.0 mM)), glucose-6-phosphate dehydrogenase (1 IU), DETAPAC (0.8 mM) and potassium phosphate buffer (50 mM, pH 8.0.). NADPH (0.5 mM) can also be added to supplement the NADPH-generating system (described above). DETAPAC is added to ensure that metal-catalyzed oxidation of protein thiols is not obtained. Even though the pH optimum is higher, non-specific oxidation of thiols occur at elevated pH, and the reaction runs at a lower pH. To initiate the reaction, cysteamine (1 mM or less) or another appropriate low molecular weight thiol is added to the mixture to generate the disulfide cystamine. After 20 mins, the protein (or peptide) (50 nM or more) is added and the reaction is allowed to continue for 1 hr at 37° C. Periodic monitoring of the reaction mixture directly by HPLC or indirectly by peptide or protein activity measurements indicates the course of protein renaturation. For example, pig liver FMO (form 1) has been shown to catalyze the cysteamine-dependent efficient renaturation of ribonuclease as determined by photometric monitoring of increasing ribonuclease activity (Poulsen and Ziegler, Arch. Biochem. Biophys. 183:563–570 (1977)). As outlined previously (Ziegler, Ann. Rev. Biochem. 54:305–329 (1985)), FMO is one of the few enzymes capable of forming disulfides in the presence of the normally reducing conditions of the cell. FMO is almost unique in excluding most physiological thiols from its active sites (Ziegler, TIPS 11:321–324 (1990)). As a consequence, cysteamine, the only currently known physiological substrate for FMO is oxidized only to the disulfide. Other endogenous thiols (such as glutathione or cysteine) which might interfere with the procedure are excluded from the active site by the enzyme. It is necessary to use an excess of the disulfide forming system with respect to protein (or peptide) to fold or renature. Under such conditions, intermolecular disulfide bond formation is facilitated and followed by rapid intramolecular disulfide bond formation. The key step shown above in the scheme is the initial selective oxidation of cysteamine to the sulfenic acid followed by rapid attack by another cysteamine to the disulfide. The feasibility of this type of reaction has been demonstrated (Decker et al., *Chem. Res. Toxicol.* 4:670–677 (1991)). The use of large scale immobilized or fluidized enzyme reactors employing HLFMO 3 enables significant quantities of native proteins to be folded and isolated in a convenient and efficient manner.

EXAMPLE 11

Characterization of Two Human FMO3 Variants

Two forms of HFMO3 found in the human population were compared. The comparison of catalytic properties was greatly facilitated by the adoption of a protein fusion expression purification system that had the added benefit of stabilizing these enzymes during expression, purification and assay. The proteins were isolated in a soluble form that greatly reduced the requirement for added detergent. It was shown that because both polymorphic enzymes are capable of oxygenating a tertiary amine, the mutation of the second form cannot be the sole reason for trimethylaminuria. However, the two enzymes do have differing substrate specificities which might affect those individuals that express only one form or the other.
Methods 10-(4-N,N-dimethylamide butyl)-2-(trifloromethyl phenothiazine). 5-bromovaleric acid (3.00 g, 16.6 mmol) was dissolved in $CH_2Cl_2$ (50 ml) and chilled in an ice bath. Dimethylamine hydrochloride (1.385 g, 17 mmol, 1.02 eq) and triethylamine (1.717 g, 17 mmol, 1.02 eq) were added to the above solution followed by the addition of DCC (3.508 g, 17 mmol, 1.02 eq). The reaction was stirred at 0° C. under an Ar atmosphere for 7 h. The reaction mixture was filtered through celite and the filtrate was concentrated in vacuo. The crude product (3.00 g, 14.4 mmol) was dissolved in anhydrous THF (50ml) followed by the addition of 2-(trifloromethyl)-phenothiozine (3.21 g, 12 mmol, 0.85 eq) and NaH (1.17 g, 60%, 29 mmol). The reaction was allowed to stir at room temp for 28 h. The reaction mixture was treated with 10% aqueous solution of HCl and extracted twice with ethyl acetate. The organic layer was dried over $Mg_2SO_4$, concentrated in vacuo, and purified by flash chromatography (silica gel ethyl acetate: hexane, 2:1 v:v) to give the product as a pale brown oil (2.58 g, 40% yield).

10-(5-N,N-dimethylaminopentyl)-2-(trifloromethyl phenothiazine). 10-(4-N,N-dimethylamide butyl)-2-(trifloromethyl phenothiazine) (0.50 g, 1.27 mmol) was dissolved in anhydrous THF (10.0 ml) followed by the addition of $LiAlH_4$ (2.54 ml of 1.0 M in THF, 2.54 mmol) under Ar atmosphere and allowed to stir at room temperature for 2 h. An aqueous solution of 10% HCl was added to the reaction mixture dropwise in order to quench excess $LiAlH_4$. Aqueous saturated $Na_2CO_3$ was added to bring the pH to 12 and the mixture was extracted twice with ethyl acetate. The combined organic layers were washed with water and brine, dried over $Mg_2SO_4$, concentrated in vacuo, and purified by flash chromatography (silica gel, 0.2% TEA 10% MeOH in $CH_2Cl_2$, $R_f$=0.15) to obtain the product as a yellow oil (0.36 g, 75% yield). $^1$H NMR: δ 1.72 (m, 4H), 2.05 (m, 2H), 2.43 and 2.44 (s, 6H), 2.48 (t, J=7.0 Hz, 2H), 4.12 (t, J=6.9 Hz, 2H), 7.13–7.39 (m, 3H), 7.41–7.43 (m, 4H). MS: 381 (MH$^+$), 280 [MH$^+$—$C_4H_8N(CH_3)_2$], 266 [MH$^+$—$C_5H_{10}N(CH_3)_2$, 248 [MH$^+$—$C_5H_{10}N(CH_3)_2F$], 114 (MH$^+$—$C_{13}H_7NSCF_3$), 84 (MH$^+$—$C_{13}H_7NSCF_3NCH_3$).

Methyl p-tolyl sulfoxide. This material was synthesized from methyl p-tolyl sulfide according to Cashman et al., supra. The product was purified by flash chromatography (silica gel, ethyl acetate, $R_f$=0.21). $^1$H NMR: δ 2.52 (s, 3H), 2.80 (s, 3H), 7.43 (d, J=7.8 Hz, 2H), 7.64 (d, J=7.3 Hz, 2H). MS: 155 (MH$^+$), 138 (M-O).

Sequencing was performed using Sanger sequencing technology. Automated electrophoresis and data recording were performed with Applied Biosystems (Foster City, Calif.) sequencer 373A.

For subcloning HLFMO3 into the maltose binding protein fusion system, two oligonucleotides were synthesized to use in PCR amplification of the HFMO3 cDNA. This allowed proper insertion of HFMO3 cDNA into the expression vector pMAL-c2 in such a way that allowed for the fusion of HFMO3 cDNA at the 3' end of sequences encoding the maltose binding protein (MBP). Oligos 5'-GGGAAGAAAGTGGCCATC-3' (SEQ ID No. 15) and 5'-CCGGTCGACGGATCCAAGCTTAGGTCAACACA AGG-3' (SEQ ID No. 16) were the 5' and 3' PCR primers, respectively. The 3' oligo includes HindIII, BamHI and SalI sites which allowed, among other manipulations, insertion of the PCR fragment into the pMAL-c2 vector between the XmnI site (blunt end) and the HindIII site. The two oligonucleotides were used in an amplification reaction with the HFMO3 cDNA-containing vector pHFMO3-fl. Approximately 0.1 μg of the single-stranded form of pHFMO3-fl was used as the template for PCR. 100 pmol of each primer was used in a 50 μl reaction under standard PCR buffer conditions. Cycle conditions were 94° C. melting, 55° C. annealing and 74° C. extension and after 20 cycles, yielded sufficient DNA to proceed with the cloning steps. The PCR product was treated with DNA polymerase I (Klenow fragment) to ensure that the DNA fragments had flush ends prior to cloning. The vector, named pMAL-HFMO3, is the result of cloning the PCR fragment into the XmnI and HindIII sites of the vector pMAL-c2. Several clones were examined for expression before one was isolated that produced a product with the expected size of the full length fusion. The junction between the maltose binding protein and HFMO3 contains a factor Xa cleavage site and is a feature of the pMAL-c2 vector. The fusion junction was designed so that cleavage of the HFMO3-MBP fusion protein with factor Xa would release an HFMO3 product that contains an amino-terminal glycine, which is the native condition of HFMO3 isolated from human liver.

The lysine 158 codon of HFMO3 is AAG. A single change to GAG converts this position to a codon for glutamate. This was accomplished by site-directed mutagenesis using the BioRad Mutagene kit. The oligonucleotide synthesized for this purpose was: 5'-CC TGG AAA GGA CT(G/C) TTT TGG TAG GTT GGG-3' (SEQ ID Nos. 17 and 18, respectively). This oligo was designed to change lysine 158 to either a glutamate or glutamine. In fact only glutamate was recovered in several attempts verified by sequencing of candidates. The mutagenesis was carried out on a subclone of HFMO3 (NcoI to SacI) in vector pGEM(−). The recovered mutation was then transferred to the MBP-fusion expression vector by exchanging the NheI to SacI fragment of the mutagenized vector with that of vector pMAL-HFMO3.

For expression of the HFMO3-MBP fusion protein and purification with amylose resin, initially, small scale preps of whole cell extract were performed to confirm the presence of the HFMO3-MBP fusion product. Sufficient full-length product was synthesized in whole cell preparations of induced cells to observe on SDS-polyacrylamide gel electrophoresis. Fusion protein preparations were performed with equal efficiency on several scales (i.e., 25 mls, 250 mls and 41). Starter cultures were grown overnight on selective (100 μg/ml ampicillin) SOC medium (Maniatis et al., 1989). The fresh overnight culture was diluted 100-fold into SOC medium with 100 μg/ml ampicillin. The culture was grown at 37° C. for 2 h with vigorous shaking. At 2 h the cultures were induced with the addition of IPTG to a final concentration of 0.6 mM and 8 mg/l riboflavin. The cultures were incubated for a further 3 hrs at 37° C. with vigorous shaking. At three hours the cells were removed from the incubator and chilled on ice. A 4 l culture was harvested at 2–4° C. by centrifugation at 6,000×g for 15 min., washed once with 400 ml column buffer (50 mM sodium phosphate buffer, pH 8.4) resuspended in 80 ml of lysis buffer (50 mM sodium phosphate, pH 8.4, 0.1% lecithin, 0.5% triton X-100, 0.5 mM PMSF). The cell resuspension was then allowed to freeze slowly at −20° C. After freezing, the cells were either transferred to −80° C. for storage or thawed prior to sonication. The freeze-thaw process seemed to improve the efficiency of lysis. Sonication was done in three bursts (60 sec, 30 sec, and 20 sec, for the 4 l preparations) with a small probe. The lysates were cleared by centrifugation at 14,000×g for 20 min. Supernatant derived from a 4 l culture was passed once through an amylose column (1.2×14 cm, bed volume about 15 mls) that was pre-equilibrated in column buffer. This column was then rinsed with 10 column volumes. This wash was sufficient to remove unbound proteins. Proteins bound by virtue of their affinity to amylose were then released with column buffer that contained 10 mM maltose. Fractions were collected and assayed for protein concentration.

For HFMO3-MBP assay, all HFMO3-MBP incubations were done as follows: Into a test tube was added DETAPAC (1.2 mM, final concentration for a 250 μl reaction) followed by the addition of 60 μl NADPH generating system (0.4 mM NADP, 0.4 mM glucose-6-phosphate, and 20 μl of a 50 units ml$^{-1}$ glucose-6-phosphate dehydrogenase). The tube was chilled on ice and buffer and enzyme were added as described below for individual experiments to give a volume of 240 μl. The incubation was initiated by the addition of 5-DTP (10 μl of 5 mM) and placed in a shaking water bath at 37° C. for 10 min (unless specified otherwise). The incubation was stopped by the addition of 1.0 ml of ice-cold $CH_2Cl_2$. Following the addition of sodium carbonate (approx. 20 mg), the culture tube was vortexed, centrifuged (2000×g, 10 min), and the organic layer was removed and transferred to a 1.5 ml microfuge tube. The organic solvent was evaporated under a stream of $Ar_{(g)}$ to dryness and the residue was taken up in MeOH (300 μl) for determination HPLC analysis.

The 5-DTP N-oxide product was resolved from the substrate by HPLC (5 μm Axxiom silica HPLC column (4.6× 250 mm), Richland Scientific, Novato, Calif.) with a Hitachi L-6200A HPLC (San Jose, Calif.) and monitored with a Hitachi L-4200 H variable wavelength UV-VIS detector set at 254 nm. Data was analyzed with a Hitachi D-2500 integrator. A mobile phase of 70% A and 30% B, where A was methanol containing 0.017% perchloric acid and B was isopropanol, was used at a flow rate of 1.5 ml min. This HPLC system efficiently resolved the 5-DTP substrate from the N-oxide product with retention times of 5.30 min and 4.30 min, respectively.

MTS-oxygenation assays were carried out under the same buffer, temperature, time and volume conditions, as for the N-oxygenation assays. The reactions were initiated upon addition of 10 μl of a 5 mM solution of MTS. The reaction was quenched with the addition of 700 μl of 80% $CH_3CN$:20% hexane then 20 mg NaCl(s) and vortexed vigorously for 10 sec. The quenched reactions were then centrifuged briefly to separate the phases. The organic layer, containing product and substrate, was removed and used directly for HPLC analysis.

The MTS S-oxide product was resolved from substrate with reverse phase HPLC on a C-18 column ((4.6×250 mm) Microsorb-MV, Rainin Instruments Co., Inc., Woburn, Mass.). All other instruments used were the same as above for the N-oxygenation reactions. Conditions for elution were 50% $CH_3CN/H_2O$ (v:v) with a flow rate gradient as follows: 1.5 ml min$^{-1}$ from 0 to 4 min., 1.5–2.5 ml min$^{-1}$ from 4 to 5 min, 2.5 ml min$^{-1}$ from 5 to 15 min. The S-oxide eluted during the first gradient phase while the substrate eluted during the last phase and were detected at 236.5 nm.

After purification of the HFMO3-MBP by amylose resin affinity chromatography, the amount of detergent present was analyzed by extraction of the protein and HPLC analysis. This was done for the glu$^{158}$-HFMO3-MBP. 185 μg of glu$^{158}$-HFMO3-MBP was placed in a typical incubation format and extracted with 1 ml acetonitrile. The organic fraction was mixed thoroughly, separated by centrifugation, evaporated to dryness and taken up in methanol for analysis by HPLC. HPLC was done with a Hitachi HPLC as described above and a C-18 Microsorb reverse phase column (Rainin, Emeryville, Calif.). An eluent of $CH_3°CN/H_2O/CH_3OH/NH_4OH$ (62:35:3:0.4; vol:vol) was used to separate Triton X-100 and other detergents (retention volume 10 ml) from other polar materials. Using a standard curve of 254 to 5088 pmol of Triton X-100 it was established that 0.89 nmol of detergent per nmol of HFMO3 was present after the amylose resin affinity chromatography step. This preparation was designated the "detergent free" HFMO3-MBP.

The requirements for additional detergent for optimal activity of the detergent free HFMO3-MBP was examined. The enzyme activity assay was essentially the same as described above with the exception that that amount of added Triton X-100 was varied from 0–0.5%.

The pH dependence of HFMO3-MBP (lys$^{158}$ and glu$^{158}$) was assayed as described above except that reaction pH conditions were varied. The pH range was adjusted by varying the ratio of stock solutions of 100 mM $K_2HPO_4$ and 100 mM $KH_2PO_4$ or 100 mM KOH to reach the desired pH. A pH range from 6.5 to 10.5 was examined. For glu$^{158}$-HFMO3-MBP 40 μl of enzyme (146.8 μg) (3.67 mg ml$^{-1}$ in 50 mM potassium phosphate buffer, pH 8.4) and 110 μl of buffer was used to make final incubation volume of 240 μl prior to the addition of substrate. For lys$^{158}$-HFMO3-MBP 25 μl of enzyme (60 μg) (3.0 mg ml$^{-1}$ in 50 mM potassium phosphate buffer, pH 8.4) and 125 μl of buffer was used. The optimum amount of Triton X-100, as determined above, was used.

Time course studies on glu$^{158}$- and lys$^{158}$-HFMO3-MBP were carried out, where incubation times varied from 0–20 min (e.g., 0, 3, 5, 10, 15, and 20 min). For glu$^{158}$-HFMO3-MBP, 10 μl of enzyme (23 μg) and 135 μl of buffer at pH 9.0 was used. For the lys$^{158}$-HFMO3-MBP, 10 μl of enzyme (30 μg) and 135 μl of buffer at pH 9.0. Optimal concentrations of Triton X-100 was added to the reactions.

To establish that activity was dependent on the amount of protein added to a reaction, a protein-dependence study was performed for both enzymes. The reactions were done as described above except the amount of enzyme varied from 0 to 100 μg for glu$^{158}$ and lys$^{158}$-HFMO3-MBP. The assay was essentially linear over a range of 20 to 70 μg enzyme.

Results from protein-dependence experiments showed that product formation was linear from 20 to 70 μg of protein for either $glu^{158}$- or $lys^{158}$-HFMO3-MBP. Results from time course experiments showed that the product formation was linear from 5 to 20 min for both $glu^{158}$- and $lys^{158}$-HFMO3-MBP. Therefore, 15 min incubation times were applied to these analysis with 30–45 µg of protein.

Results

Expression from the pMAL-c2 derived HFMO3 fusion vectors resulted in considerable overproduction of full length HFMO3-MBP and several other different sized proteins that were retained on the amylose affinity resin. The sizes of these products range from approximately 100 kD (the expected size of the full length fusion product) to approximately 43 kD. These products were present only in cells that contain the fusion vector and were not seen in cells without a vector or with the pMAL-c2 vector (which produces maltose binding protein exclusively as the only amylose binding protein). The common property of these proteins is that they bind to the amylose resin and are specifically released by maltose. It was assumed that these proteins are all the result of expression from the HFMO3-MBP vector, contain the maltose binding protein domain and arise either through proteolytic breakdown of the full length protein or, more likely, are the result of incomplete translation because the SDS-PAGE pattern observed and the relative intensity of the bands was almost always identical from prep to prep, implying an inherent stability of the products in cells or cell extracts. Purification of the maltose binding domain fusion proteins was possible in one step using amylose resin. There was a dramatic increase in specific activity for the conversion of 5-DTP to 5-DTP N-oxide after this step. Further fractionation of the MBP-containing species on the basis of size indicated that the bulk of the HLFMO3 oxygenation activity was associated with the full length product, although the 60 kD protein associated strongly with the full length protein. Based on the performance of the Sephacryl S-300, the active fraction elutes earlier, and is apparently much larger than expected for a 100 kD protein. This suggests that the active form of the enzyme is in a higher ordered complex. In addition to aiding in the purification of HFMO3 enzyme, the addition of the maltose binding protein domain to the amino terminus of HFMO3 clearly stabilized the enzyme when compared to enzyme purified from liver microsomes or produced as a non-fusion protein in E. coli.

Figure 6A:
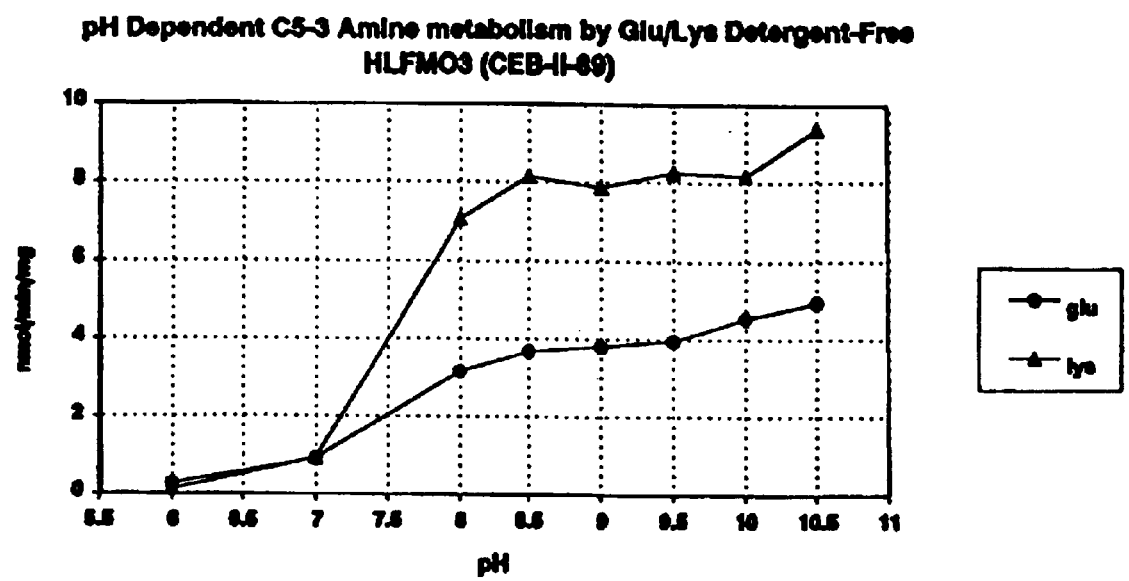
FIG. 6A shows pH requirements for HFMO3-MBP activity.
Figure 6B:
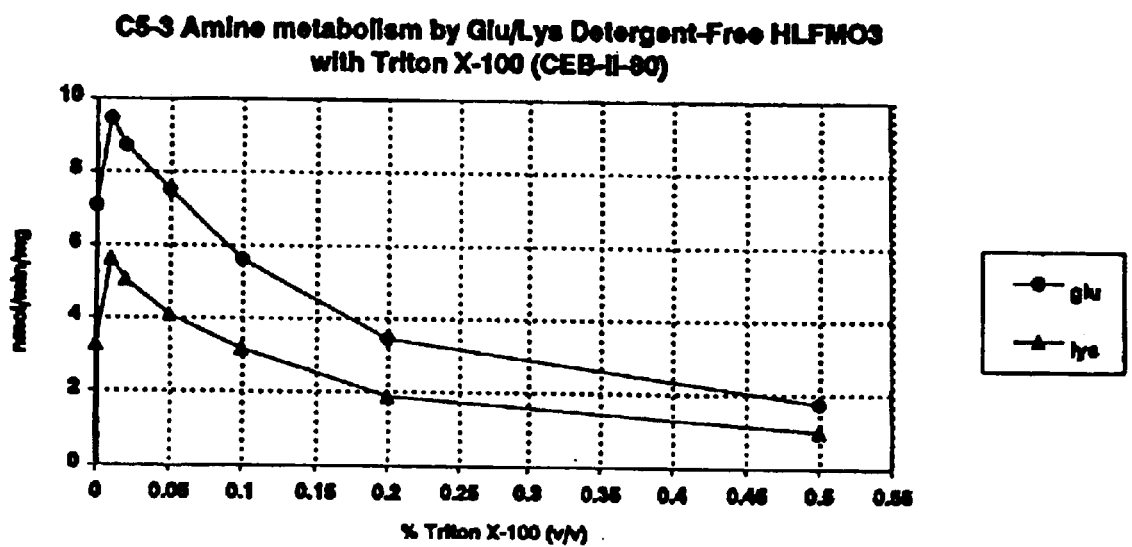
FIG. 6B shows detergent requirements for HFMO3-MBP activity.

For the pH and detergent requirements for maximal HFMO3-MBP activity, FIG. 6A reveals a parallel behavior of 5-DTP N-oxygenation activity in response to changing pH for both the lys and glu forms of HFMO3-MBP. For both enzymes there was little or no activity below pH 7.0 with a marked increase from pH 7.0 to 8.0. Thereafter a gradual increase in activity was observed. FIG. 6B shows that the maximal N-oxygenation activity of both forms of the enzyme was with 0.015. N Triton X-100 (v:v) added. While the preparation of these enzymes included an extensive detergent free wash of the protein, while bound to the affinity matrix, some detergent remains associated with the protein upon elution from the amylose resin (as determined by HPLC). The amount of detergent remaining with detergent depleted enzyme is not enough for maximal activity. An increase of added detergent beyond 0.05% had a profound negative effect on enzyme activity, especially at 0.5%. These concentrations of Triton X-100 are far lower than commonly used (i.e. 1%) for most preparations of FMO enzymes analyzed.

Kinetic constants for 5-DTP oxygenation in the presence of $lys^{158}$ or $glu^{158}$-HFMO$_3$-MBP were determined from Lineweaver-Burke analysis and listed in Table 6. The $glu^{158}$ variant displayed a much greater maximal velocity for the oxygenation of 5-DTP. $Glu^{158}$-HFMO3-MBP displayed a slightly higher $K_m$ for this substrate than $lys^{158}$-HFMO3-MBP, although some variation was observed in the activities for both forms of the enzyme, depending on the preparation, but the differences were greater than can be explained by this effect.

TABLE 6

Kinetics data for 5-DTP as substrate with $glu^{158}$- and $lys^{158}$-HFMO3-MBP

| Enzyme | $V_{max}$ (nmole/min/nmol of flavin) | $K_m$ (µM) | r (coeff.) |
|---|---|---|---|
| $glu^{158}$-HFMO3-MBP | 15.8 | 108 | 0.99 |
| $lys^{158}$-HFMO3-MBP | 1.88 | 78 | 0.98 |

Both HFMO3-MBP variants, $glu^{158}$ and $lys^{158}$, were examined for 5-DTP tertiary amine N-oxygenation and MTS sulfide S-oxygenation in parallel to compare the relative activities between the two enzyme variants and to avoid the problem of any apparent differences that might arise from variations due to enzyme preparation effects. For the $glu^{158}$-HFMO3-MBP (1.5 mg of protein $ml^{-1}$ or 2.1 µg of flavin ml in 50 mM potassium phosphate buffer, pH 8.4) 30 µg (20 µl) of the protein was used per incubation and 130 µl of buffer at pH 9.0 (50 mM) was used to make a final incubation volume of 240 µl prior to the addition of substrate. For the $lys^{158}$-HFMO3-MBP (3.0 mg of protein ml–1 or 3.6 µg of flavin ml–1 in 50 mM potassium phosphate buffer, pH 8.4) 45 µg (30 µl) of protein was used per incubation and 120 µl of buffer at pH 9.0 (50 mM) was used to make a final incubation volume of 240 µl per incubation. MTS was a far better substrate for both enzymes. It was striking that $glu^{158}$-HFMO3-MBP enzyme was much better able to discriminate between the tertiary amine and the sulfide substrates.

Thus, the maltose binding domain fusion system appears to be an ideal expression system for the production of highly active HFMO3. The MBP fusion allows for an efficient first step purification procedure that yields enzyme in a substantially purified and active state. In addition, fusion of the MBP domain to HFMO3 reduces the detergent requirement for activity and the protein itself is now obtained in a soluble state. This is important because soluble HFMO3-MBP (as opposed to the microsomal enzyme) can be further purified efficiently with additional steps of fractionation, including size exclusion chromatography.

The HFMO3-MBP expression system is also adaptable to the expression of mutant enzymes. Two variants of HFMO3-MBP can be expressed in active form and characterized in detail because of the virtues of high expression, ease in purification and stabilized activity while in a soluble state. The two forms of HFMO3, differing at position 158, were analyzed with respect to their ability to oxygenate a tertiary amine and a sulfide-containing substrate. Both forms of go HFMO3-MBP, $lys^{158}$ and $glu^{158}$, were active against both substrates.

Regarding possible differences between $lys^{158}$- and $glu^{158}$-HFMO3-MBP parallel assays against both substrates revealed that $lys^{158}$- and $glu^{158}$-HFMO3-MBP have different capabilities to discriminate between the two substrates.

$Glu^{158}$ has a much greater relative activity towards the sulfide (20-fold), comparing MTS vs. 5-DTP activity, than does $lys^{158}$ (4.9-fold).

EXAMPLE 12

N-Oxygenation of Endogenous Amines as Bioindicators of Human Disease

The cDNA-expressed human FMO3-maltose binding protein (FMO3-MBP) efficiently catalyzes the sequential N-oxygenation of primary amines to oximes through the intermediacy of hydroxylamines. Thus, 10-(N-n-octylamino)-2-(trifluoromethyl)phenothiazine is stereoselectively converted to the cis oxime via the intermediate hydroxylamine as determined by the analysis of metabolic extracts by HPLC. A similar product stereoselectivity was observed in the presence of human liver microsomes. Studies on the biochemical mechanism of oxime formation suggests that cis-oxime formation is largely dependent on human FMO3 activity. In addition, formation was not dependent on autoxidation of hydroxylamines or generation of oxygen radical species. Thus, $H_2O$, $OH^+$ and $O_2^-$ had virtually no effect on the formation of oxime from the primary hydroxylamine. This result is in contrast to what has been reported for other forms of FMO (i.e., FMO1) (Rauckman et al., *Mol Pharmacol.* 15, 131–137 (1979)) and suggests that FMO3 possesses an intrinsic ability to avoid oxygen radical-mediated substrate oxygenations. This represents a fundamental difference between FMO3 and other FMOs and indicates a use of FMO3 as a stereoselective catalyst in the formation of precious chemicals or hard to form metabolites having great stereochemical purity.

Similarly, the biogenic amine phenethylamine is stereoselectively converted to trans oximes in the presence of adult human liver microsomes and cDNA-expressed human FMO3-MBP via the intermediacy of the hydroxylamine as determined by analysis of metabolic extracts by HPLC. Studies of the effect of metabolic inhibitors on oxime formation suggested that adult human liver microsomal FMO3 is largely responsible for trans oxime formation. It is notable that in the adult human liver microsomes examined, there is more than a 6-fold increase in the efficiency of forming oximes compared with pig liver microsomes. This is surprising in light of the fact that pig liver microsomes are generally 1 to 15-fold more active at FMO-mediated formation of tertiary amine N-oxides compared to FMO-mediated formation of tertiary amine N-oxides in adult human liver microsomes. Thus, the prominent FMO enzyme form in pig liver microsomes (i.e., FMO1) is about 60 to 100-fold less active than the major form of FMO in adult human liver microsomes (i.e., FMO3) at forming oximes from primary amines. Depending on the substrate and the source of FMO1, large concentrations of primary amines (i.e., n-octylamine) have been observed to stimulate FMO-like activity. Both variants of human FMO3 (i.e., Lys 158 and Glu 158 variants) were approximately equally efficient at stereoselectively forming trans phenethylamine oxime from phenethylamine (i.e., 3.2±0.4 and 4.9±0.6 nmol trans oxime formed/min/mg of protein, respectively). To confirm the intermediacy of the hydroxylamine metabolite as an obligatory intermediate in the formation of trans oxime, the conversion of phenethyl hydroxylamine to oxime was examined in the presence of human cDNA-expressed FMO3-MBP variants. Similar to phenethylamine, phenethyl hydroxylamine was stereoselectively converted to the trans oxime by human FMO3-MBP variants Lys 158 and Glu 158 (i.e., 3.4±0.3 and 4.5±0.8 nmol trans oxime formed/min/mg of protein, respectively). Formation of oxime product was not a consequence of autooxidative or oxygen radical participation because H2O2, OH(and O2-made very little contribution to oxime formation. The use of cDNA-expressed human FMO3 will permit the production of unusual or rare nitrogen-, sulfur-, phosphorous- and other heteroatom-containing chemicals and metabolites possessing a great degree of stereochemical purity. In addition, the observations about biogenic amine metabolism by human FMO3 indicates that FMO3 plays a novel role in amine metabolism and cellular homeostasis. Generation of novel biogenic amine metabolites with pharmacological activity in their own right or truncation or abrogation of biological activity of biogenic amines by the action of FMO3 suggests that FMO3 activity may participate in controlling a number of fundamentally important biochemical pathways. Analysis for the formation or lack of formation of the FMO3-mediated biogenic amine metabolites in humans may serve as a bioindicator of some fundamental abnormality associated with cardiovascular, central nervous system or some other state associated with biogenic amine metabolism.

EXAMPLE 13

Bioindicators of Human FMO3 Activity

Two reliable methods enable the non-invasive determination of human FMO3 activity in adult humans or children. Determination of the amount and stereoselectivity of trans (S)-nicotine N-1'-oxide formation in human urine at steady state allows the unambiguous determination of the FMO3 activity (Park et al., *Chem. Res. Toxicol.* 6:880–888 (1993)). Previously, it had been shown that in vitro, (S)-nicotine is exclusively converted to trans (S)-nicotine N-1'-oxide by the action of human FMO3 (Cashman et al., *Chem. Res. Toxicol.* 5: 639–646 (1992)). Because neonatal liver has predominantly FMO1 as the major FMO present, and because FMO1 converts (S)-nicotine to a 57:43 ratio of trans to cis (S)-nicotine N-1'-oxide (Cashman et al., *Chem Res. Toxicol.* 5:639–646 (1992); Damani et al., *Mol Pharmacol.* 33:702–705), detection of cis (S)-nicotine N-1'-oxide serves as a highly selective means of determining FMO1 activity. This may be extremely useful in the determining the amount of FMO1 in neonatal or adult human liver. Because FMO1 presence in adult human liver would represent an abberation from the normal condition of almost predominant presence of FMO3 this would indicate hepatic neoplasm or other related cancerous condition. Thus, stereoselective analysis of N-oxide metabolites could provide a convenient method to phenotype humans for FMO1 and FMO3 activity. Metabolic phenotyping can be validated by selective hybridization of pre-mRNA, RNA or DNA as well as other quantification involving selective immunoabsorption tests. Not all humans ingest (S)-nicotine and while (S)-nicotine-N-1'-oxide metabolites are a useful bioindicator of FMO activity, a second analytical method was developed with more widespread application.

Trimethylamine is commonly ingested in foodstuffs or it is available in the diet of humans from choline and other sources. Trimethylamine (TMA) is exclusively eliminated in humans by metabolism to trimethylamine N-oxide (TMANO). Using the cDNA-expressed human FMO3-maltose binding protein (i.e., FMO3-MBP) it has been determined that both the Lys 158 variant and the Glu 158 variant N-oxygenate TMA to its N-oxide. Using evaporative light scattering HPLC detection and following the general metabolic incubation conditions described herein for FMO3, it has been established that the Km is 634 uM and the Vmax is 3.8 nmol of TMANO formed/min/mg of protein for the Lys 158 variant. Similar values were also observed for the Glu 158 FMO3 variant. The results, suggest that human FMO3 is exclusively responsible for the N-oxygenation of TMA in humans. Thus, urinary TMANO formation provides a simple, reliable and direct assay of FMO3 activity in adult humans. Analysis of TMA to TMANO ratios provides a direct means of phenotyping adult humans for FMO3 activity. Phenotyping FMO3 activity in humans would provide a simple means of evaluating the relationship between the presence of FMO3 and various disease conditions. For example, individuals deficient in FMO3 would be predicted to have trimethylaminuria. In addition, because FMO3 is recognized to N-oxygenate biogenic amines such as phenethylamine (and presumably tyramine, dopamine, norepinephrine, serotonin and other neurotransmitters and neuroexcitatants including glutamine, polyamines and other pharmacologically important amines), it is likely that humans with deficiency of FMO3 will also have abnormal biogenic or other amine metabolism and suffer significant disease states as a consequence (i.e., cardiovascular diseases, central nervous system diseases and other neurological conditions). Evaluation of humans for unusual FMO3-mediated metabolites could provide an early bioindicator of a disease condition such as hypertension or other disease condition.

Example 14

Selective Screening of Anti-bacterial Activity

As described above, FMO1 and FMO3 possess distinct substrate specificities. One of the best functional groups for N-oxygenation substrate activity is the basic tertiary amine of a piperidine moiety, for example. FMO1 (Cashman and Ziegler, *Mol. Pharmacol.* 29:163–167 (1986)) and FMO3 (Lomri et al., *Chem Res. Toxicol.* 6:800–807) metabolize basic tertiary amine centers to tertiary amine N-oxides to form highly polar metabolites. Oftentimes the N-oxide metabolite possesses substantially less biological activity than the parent tertiary amine. Recognizing that many of the quinoline antibiotics possess piperidine functional groups, it was reasoned that if FMO N-oxygenated the antibiotic to form the tertiary amine N-oxide, this could be used as a selection method to isolate new FMOs expressed in bacteria or other prokaryotes. For example, difloxacin is highly toxic to the NM522 *E. coli* that was used to express FMO cDNA (i.e., bactericidal action EC50 of about 5 micrograms per mL in liquid culture). In contrast, 50 or 100 micrograms, per mL difloxacin terminal tertiary amine N-oxide (synthesized and completely characterized by spectral means) is not significantly cytotoxic to NM522 *E. coli*. Depending on the FMO cDNA that has been inserted into NM522 or other *E. coli*, a remarkable cytoprotection is observed when the bacteria are grown in the presence of difloxacin. To validate the observations made in liquid culture, agar plate experiments were done in the presence of difloxacin with different strains streaked out containing different FMO cDNAs. At 0.25 microgram/mL, the plasmid containing FMO1 conferred resistance. Strains that contained FMO3 cDNA were much more sensitive under the same conditions. This is a general effect for many quinoline antibiotics that possess a strongly basic tertiary amine center. For FMOs that are capable of metabolizing antibiotics to polar, biologically inactive tertiary amine N-oxides such as the broad substrate FMO1, screening FMO1 variants obtained by random or discrete mutagenesis for their ability to N-oxygenate quinoline antibiotics could provide useful new enzymes with enhanced or new catalytic properties. Screening FMO variants that have been constructed by random or discrete mutagenesis or by other recombinant means that possess more restricted substrate specificity (such as FMO3) provides a convenient way to obtain new FMO3 enzymes with extended substrate specificity or some other useful catalytic or physical property. On the other hand, if mutagenized FMO cDNA provides enzymes (such as FMO3) that are more sensitive to an antibiotic, this could also provide a means to isolate clones of FMO proteins that confer some unusual or improved catalytic or physical property to the FMO. By using an iterative screening and selection procedure either in liquid or plate culture, novel FMO enzymes can be created by mutagenesis (e.g., possessing 90% or greater homology with the parent cDNA) that possess important new catalytic and/or physical chemical properties.

EXAMPLE 15

Antibody to FMO3

Human FMO3-maltose binding protein (FMO3-MBP) was isolated by amylose affinity gravity chromatography. From a 4 liter bacterial preparation, approximately 50 mg of highly active FMO3 protein was isolated. After selective precipitation with 14% PEG 8000 and size exclusion column chromatography on Sepharose 300, a homogenous preparation of FMO3-MBP was obtained as revealed by polyacrylamide gel electroporesis. The protein was dialyzed three times against 20 mM potassium phosphate buffer and concentrated with an Amicon Centricon apparatus by centrifugation. The protein was emulsified in Freund's adjuvant and injected into rabbits to procure antisera. Western blot analysis showed that the polyclonal antisera selectively immunostained human FMO3 either from human liver microsomes or cDNA expressed protein. Monoclonal antibodies can be prepared from the spleens of animals immunized with FMO3. With either the polyclonal or the monoclonal antibodies in hand, routine immunoblotting of human FMO3 or human liver microsomes (or other tissues) is performed using standard conditions to afford a rapid and selective method to quantify the amount of FMO3 in any tissue preparation examined. This has applications in, for example, phenotyping tissue preparations for FMO3 concentrations that can be related to catalytic activity. These find use in developing in vitro correlations between metabolic activity (e.g., N- , or S-oxygenation of a chemical or a drug) and the amount of immunoreactive and catalytic FMO3 present in a particular sample.

As will be apparent to those skilled in the art in which the invention is addressed, the present invention may be embodied in forms other than those specifically disclosed above without departing from the spirit or essential characteristics of the invention. The particular embodiments of the present invention described above, are, therefore, to be considered in all respects as illustrative and not restrictive. The scope of the present invention is as set forth in the appended claims rather than being limited to the examples contained in the foregoing description.

What is claimed is:

1. An isolated DNA sequence encoding an adult human liver flavin-containing monooxygenase (FMOS), wherein the DNA sequence is as depicted as SEQ ID NO: 5.

2. A procaryotic or eucaryotic host cell containing a DNA sequences according to claim 1 with a heterologous regulatory control sequence in an expression vector therefor.

3. An isolated DNA sequence encoding an adult human liver flavin-containing monooxygenase (FMOS), wherein the DNA sequence is as depicted as SEQ ID NO: 7.

4. A procaryotic or eucaryotic host cell containing a DNA sequence according to claim 3 with a heterologous regulatory control sequence in an expression vector therefor.

* * * * *